(12) United States Patent
Buchardt et al.

(10) Patent No.: US 8,586,532 B2
(45) Date of Patent: Nov. 19, 2013

(54) METHOD FOR SELECTIVELY MODIFYING A PROTEIN VIA TRANSGLUTAMINASE CATALYZED REACTION

(75) Inventors: Jens Buchardt, Copenhagen K (DK); Nils Langeland Johansen, Copenhagen Oe (DK)

(73) Assignee: Novo Nordisk Healthcare A/G, Zurich (CH)

( * ) Notice: Subject to any disclaimer, the term of this patent is extended or adjusted under 35 U.S.C. 154(b) by 455 days.

(21) Appl. No.: 12/674,291

(22) PCT Filed: Aug. 25, 2008

(86) PCT No.: PCT/EP2008/061082
§ 371 (c)(1),
(2), (4) Date: Jul. 9, 2010

(87) PCT Pub. No.: WO2009/027369
PCT Pub. Date: Mar. 5, 2009

(65) Prior Publication Data
US 2011/0269182 A1    Nov. 3, 2011

Related U.S. Application Data

(60) Provisional application No. 60/957,732, filed on Aug. 24, 2007.

(51) Int. Cl.
| | | |
|---|---|---|
| C07K 17/06 | (2006.01) | |
| C07K 17/08 | (2006.01) | |
| C07K 14/61 | (2006.01) | |
| C07K 14/62 | (2006.01) | |
| A61K 38/05 | (2006.01) | |
| A61K 38/27 | (2006.01) | |
| A61K 38/28 | (2006.01) | |
| C12P 21/02 | (2006.01) | |

(52) U.S. Cl.
USPC ........... 514/9.7; 514/6.9; 514/11.3; 514/11.4; 530/399; 530/402; 435/68.1

(58) Field of Classification Search
None
See application file for complete search history.

(56) References Cited

U.S. PATENT DOCUMENTS

| 4,179,337 A | 12/1979 | Davis et al. | |
|---|---|---|---|
| 2007/0105770 A1* | 5/2007 | Johansen et al. | 514/12 |

FOREIGN PATENT DOCUMENTS

| EP | 0950665 | 10/1999 |
|---|---|---|
| WO | WO 2005/070468 | 8/2005 |
| WO | WO 2008/101957 | 8/2008 |

OTHER PUBLICATIONS

NCBI listing for Transglutaminase from S. mobaraensis; accessed Feb. 8, 2013.*
Chica, R.A. et al., "Tissue Transglutaminase Acylation: Proposed Role of Conserved Active Site Tyr and Trp Residues Revealed by Molecular Modeling of Peptide Substrate Binding", Protein Science, 2004, vol. 13, pp. 979-991.
Nieuwenhuizen, W.F. et al., "Transglutaminase-Mediated Modification of Glutamine and Lysine Residues in Native Bovine β-Lactoglobulin", Biotechnology and Bioengineering, 2004, vol. 85, No. 3, pp. 248-258.
Ohtsuka, T. et al., "Comparison of Substrate Specificities of Transglutaminase Using Synthetic Peptides as Acyl Donors", Bioscience, Biotechnology, Biochemistry, 2000, vol. 64, No. 12, pp. 2608-2613.
Pasternack, R. et al., "A Fluorescent Substrate of Transglutaminase for Detection and Characterization of Glutamine Acceptor Compounds", Analytical Biochemistry, 1997, vol. 249, pp. 54-60.
Sato, H., "Enzymatic Procedure for Site-Specific Pegylation of Proteins", Advanced Drug Delivery Reviews, 2002, vol. 54, pp. 487-504.
Wada, E. et al., "Enzymatic Modification of β-Lactoglobulin with N-Fatty-Acyl-Dipeptide by Transglutaminase from *Streptomyces mobaraense*", Biotechnology Letters, 2001, vol. 23, pp. 1367-1372.

* cited by examiner

*Primary Examiner* — Kevin S Orwig
(74) *Attorney, Agent, or Firm* — Jianjie Hu

(57) ABSTRACT

The present invention relates generally to a novel method of introducing property modifying groups to a protein. In particular, the present invention relates to the derivatization of lysine residues, as well as new conjugates of growth hormones with improved pharmacological properties, and methods for their preparation and use in therapy.

20 Claims, 4 Drawing Sheets

Glutamine in a protein

SEQUENCE LISTING

<160> NUMBER OF SEQ ID NOS: 4

<210> SEQ ID NO 1
<211> LENGTH: 654
<212> TYPE: DNA
<213> ORGANISM: Homo sapiens

<400> SEQUENCE: 1

```
atggctacag gctcccggac gtccctgctc ctggcttttg gcctgctctg cctgccctgg      60
cttcaagagg gcagtgcctt cccaaccatt cccttatcca ggcttttgtga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaaggcat ccaaacgctg atggggaggc tggaagatgg cagcccccgg     480
actgggcaga tcttcaagca gacctacagc aagttcgaca caaactcaca acgatgac       540 gcactactca agaactacgg gctgctctac tgcttcagga aggacatgga caaggtcgag     600
acattcctgc gcatcgtgca gtgccgctct gtggagggca gctgtggctt ctag            654
```

<210> SEQ ID NO 2
<211> LENGTH: 217
<212> TYPE: PRT
<213> ORGANISM: Homo sapiens

<400> SEQUENCE: 2

```
Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60
```

```
Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Gly Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 3
<211> LENGTH: 202
<212> TYPE: PRT
<213> ORGANISM: Homo sapiens

<400> SEQUENCE: 3

Met Ala Ala Gly Ser Arg Thr Ser Leu Leu Leu Ala Phe Gly Leu Leu
  1               5                  10                  15

Cys Leu Ser Trp Leu Gln Glu Gly Ser Ala Phe Pro Thr Ile Pro Leu
                 20                  25                  30

Ser Arg Leu Phe Asp Asn Ala Met Leu Arg Ala Arg Arg Leu Tyr Gln
             35                  40                  45

Leu Ala Tyr Asp Thr Tyr Gln Glu Phe Asn Pro Gln Thr Ser Leu Cys
 50                  55                  60

Phe Ser Glu Ser Ile Pro Thr Pro Ser Asn Arg Val Lys Thr Gln Gln
 65                  70                  75                  80

Lys Ser Asn Leu Glu Leu Leu Arg Ile Ser Leu Leu Leu Ile Gln Ser
                 85                  90                  95

Trp Leu Glu Pro Val Gln Leu Leu Arg Ser Val Phe Ala Asn Ser Leu
            100                 105                 110

Val Tyr Gly Ala Ser Asp Ser Asn Val Tyr Arg His Leu Lys Asp Leu
        115                 120                 125

Glu Glu Gly Ile Gln Thr Leu Met Trp Arg Leu Glu Asp Gly Ser Pro
    130                 135                 140

Arg Thr Gly Gln Ile Phe Asn Gln Ser Tyr Ser Lys Phe Asp Thr Lys
145                 150                 155                 160

Ser His Asn Asp Asp Ala Leu Leu Lys Asn Tyr Gly Leu Leu Tyr Cys
                165                 170                 175

Phe Arg Lys Asp Met Asp Lys Val Glu Thr Phe Leu Arg Ile Val Gln
            180                 185                 190

Cys Arg Ser Val Glu Gly Ser Cys Gly Phe
        195                 200

<210> SEQ ID NO 4
<211> LENGTH: 191
```

```
<212> TYPE: PRT
<213> ORGANISM: Homo sapiens

<400> SEQUENCE: 4

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

US 8,586,532 B2

METHOD FOR SELECTIVELY MODIFYING A PROTEIN VIA TRANSGLUTAMINASE CATALYZED REACTION

FIELD OF THE INVENTION

The present invention relates generally to a novel method of introducing property modifying groups to a protein. In particular, the present invention relates to the derivatization of lysine residues, as well as new conjugates of growth hormones with improved pharmacological properties, and methods for their preparation and use in therapy.

BACKGROUND OF THE INVENTION

It is well-known to modify the properties and characteristics of proteins by conjugating groups to the protein in order to change the properties of the protein. In fact, more than twenty years ago, U.S. Pat. No. 4,179,337 taught proteins conjugated to polyethylene or polypropylene glycols. Generally, such conjugation generally requires some functional group in the protein to react with another functional group in a conjugating group. Typically, amino groups, such as the N-terminal amino group or the 8-amino group in lysines, have been used in combination with a suitable acylating reagent. It is often desired or even required to be able to control the conjugation reaction, i.e. to control where the conjugating compounds are attached and to control how many conjugating groups are attached. This is often referred to as specificity or selectivity.

However, the repertoire of selective chemical reactions is very limited. An alternative is, by recombinant methods, to introduce special unnatural amino acids having a unique reactivity and then exploit this reactivity in the further derivatization. An alternative is to use enzymes which recognize structural and functional features of the protein to be modified. An example of this is the use of microbial transglutaminase (mTGase) to selectively modify Gln residues in growth hormone. Specifically, transglutaminase has been used in the food industry and particular in the diary industry to cross-bind proteins. Other documents disclose the use of transglutaminase to alter the properties of physiologically active proteins. See e.g. EP 950665, EP 785276 and Sato, *Adv. Drug Delivery Rev.*, 54, 487-504 (2002), which disclose the direct reaction between proteins comprising at least one Gln and amine-functionalised PEG or similar ligands in the presence of transglutaminase; see also Wada in *Biotech. Lett.*, 23, 1367-1372 (2001), which discloses the direct conjugation of β-lactoglobulin with fatty acids by means of transglutaminase. The reaction catalysed by the transglutaminase is a transamidation reaction in which the primary amide of the glutamine residue is converted to a secondary amide from a primary amine present in the reaction mixture, as shown in FIG. 1.

However, selective derivatization of proteins is a very difficult task; the derivatization of lysines in a protein by acylation is an even more inherently non-selective process. Thus, there is at present no efficient method for the selective derivatisation of lysine residues. Accordingly, there is an immediate need in the art for methods of selectively derivatizing amino acid residues such as lysine in proteins or polypeptides of interest.

DETAILED DESCRIPTION OF THE INVENTION

The present invention addresses these needs by providing a method of introducing property modifying groups to a target protein in a more selective manner via an auxiliary protein, while using conventional chemical methods. In general the method can be described as follows: first, an activated complex between the auxiliary protein and the property modifying group is formed; second, the modifying group is transferred from the activated complex to the protein to be modified in a much more selective manner than that which could be achieved by conventional methods and thus resulting in a "modified protein." As such, a "modified protein" as used herein, refers to a protein or polypeptide that has been selectively modified by a method of the invention.

Figure 2:
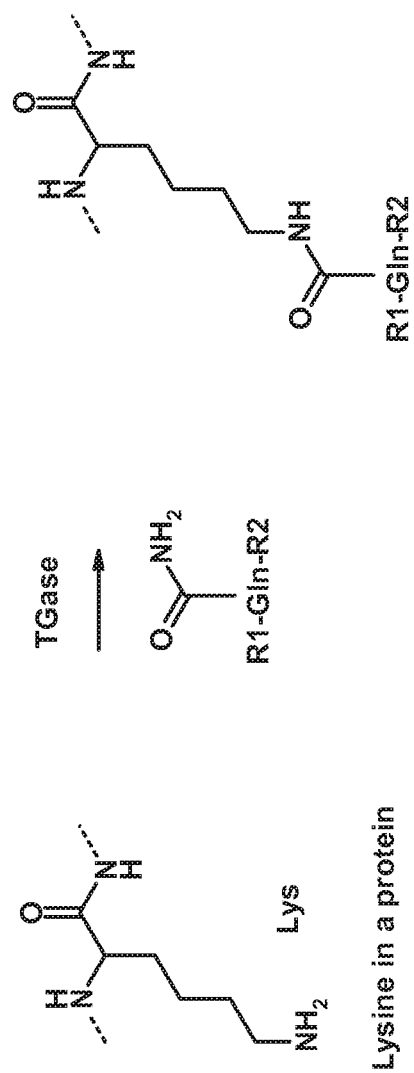
FIG. 2 depicts the general reaction of the present invention, also known as "reverse TGase.

Specifically, the present invention is directed to a method comprising a transglutaminase catalysed reaction of a protein containing at least two lysines with a property modifying group. The property modifying group is a glutamine-glycine-containing protein of the formula R1-Gln-Gly-R2. Specifically, in this process, an activated acyl complex is formed by reacting the glutamine residue in the property modifying group with TGase in order to attach the property modifying group. In a preferred embodiment, the property modifying group is transferred by acylation to a lysine residue in the target protein as depicted in FIG. 2. In one embodiment, R1 and R2 are desired substituents, where at least one of them comprises a chemical group that is suitable for further modification. Thus, the present invention involves a "reverse" TGase reaction in order to selectively modify a lysine residue within a target protein.

As used herein, the term "polypeptide" refers to a polymer of amino acid residues joined by peptide bonds, whether produced naturally or synthetically. Polypeptides of less than about 10 amino acid residues are commonly referred to as "peptides." The term "peptide" is intended to indicate a sequence of two or more amino acids joined by peptide bonds, wherein said amino acids may be natural or unnatural. The term encompasses the terms polypeptides and proteins, which may consists of two or more peptides held together by covalent interactions, such as for instance cysteine bridges, or non-covalent interactions. A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. A protein or polypeptide encoded by a non-host DNA molecule is a "heterologous" protein or polypeptide. An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms. The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

Auxiliary Proteins of the Invention

Figure 1:
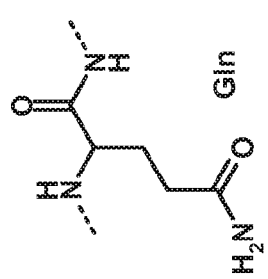
FIG. 1 depicts the general reaction catalyzed by TGase.
Figure 1:
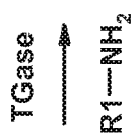
Figure 1:
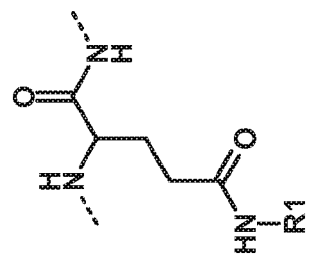

One aspect of the invention is directed to a method for selectively modifying a target protein using an auxillary protein. In a preferred embodiment, the auxillary protein is an enzyme such as transglutaminase. Transglutaminase (also interchangeably referred to herein as "TGase") is also known as protein-glutamine-γ-glutamyltransferase and catalyzes the acyl transfer reaction between the γ-carboxyamido group of a glutamine (Gln) residue in protein or a protein chain and the ε-amino group of a lysine (Lys) residue or various alkylamines, as shown in FIG. 1. TGase is widely found in various animal tissues, blood cells, blood plasma and the like, in various molecular forms. This enzyme catalyzes the cross-linking reaction through the ε-(γ-glutamyl) lysine-isoprotein bond, and cross-linking fibrin molecules at the last step in blood coagulation, as well as it is found to be concerned with keratinization of epidermis cells, coagulation of seminal fluid, healing of wounded tissues, and the like. Since transglutaminase has a very high substrate specificity to the Gln residue, there is a possibility that only certain Gln residues in the protein may be modified with an alkylamine. E.g., an alkylamine having a terminal sugar unit was introduced into .beta.-casein at its certain Gln residue(s), with the use of transglutaminase (TGase) originating from guinea pig liver (Yan, S. C. B. et al, (1984) Biochemistry, 23, 3759-3765). Furthermore, a lower molecular weight spermine derivative was introduced into apolipoprotein B at its Gln residue(s), with the use of blood coagulation factor XIII (Factor XIII), a transglutaminase found in blood plasma (Cocuzzi, E. et al, (1990), Biochem. J., 265, 707-713).

The transglutaminase to be used in the methods of the present invention can be obtained from various origins with no particular limitation, such as from various animal tissues, blood plasma components, and microorganisms. Examples of useful transglutaminases include microbial transglutaminases, such as e.g. from *Streptomyces mobaraense, Streptomyces cinnamoneum* and *Streptomyces griseocarneum* (all disclosed in U.S. Pat. No. 5,156,956, which is incorporated herein by reference), and *Streptomyces lavendulae* (disclosed in U.S. Pat. No. 5,252,469, which is incorporated herein by reference) and *Streptomyces ladakanum* (JP2003199569, which is incorporated herein by reference). It should be noted that members of the former genus *Streptoverticillium* are now included in the genus *Streptomyces* [Kaempfer, *J. Gen. Microbiol.*, 137, 1831-1892, 1991]. Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacillus lydicus*) and WO 96/22366, both of which are incorporated herein by reference. Useful non-microbial transglutaminases include guinea-pig liver transglutaminase, and transglutaminases from various marine sources like the flat fish *Pagrus major* (disclosed in EP-0555649, which is incorporated herein by reference), and the Japanese oyster *Crassostrea gigas* (disclosed in U.S. Pat. No. 5,736,356, which is incorporated herein by reference).

Thus, in a preferred embodiment, the TGase used in the methods of the invention is a microbial transglutaminase. In a more preferred embodiment, the TGase is from *S. mobaraense*. In another embodiment, the TGase is a mutant TGase having at least 80% sequence homology with native TGase.

Property Modifying Groups

Property modifying groups of the present invention encompass glutamine-containing proteins of the general formula: R1-Gln-Gly-R2. In a more preferred embodiment, the property modifying group has the formula:

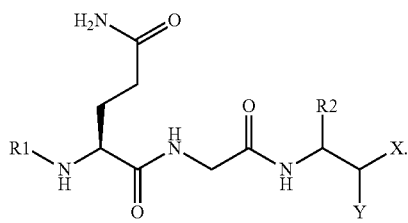

In preferred embodiments, R1 is

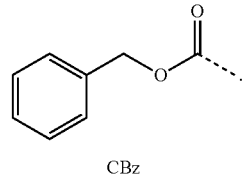

CBz

In another embodiment, R1 is CBz; R2 is selected from H, propargyl or 4-aminobenzyl; Y is OH or =O; and X is CH$_2$OH or OH.

In still another embodiment, R1 is CBz; R2 is H; Y is OH; and X is CH$_2$OH.

In yet another embodiment, R1 is CBz; R2 is 4-aminobenzyl; Y is =O; and X is OH.

In another embodiment, R1 is CBz; R2 is propargyl; Y is =O; and X is OH.

Thus, preferred property modifying groups (or substrates) of the invention are selected from the group consisting of:

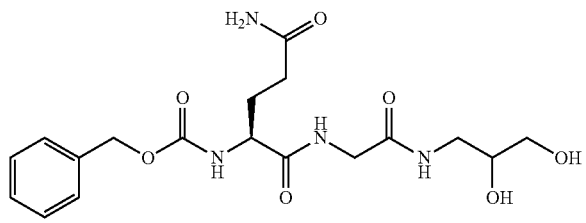

-continued

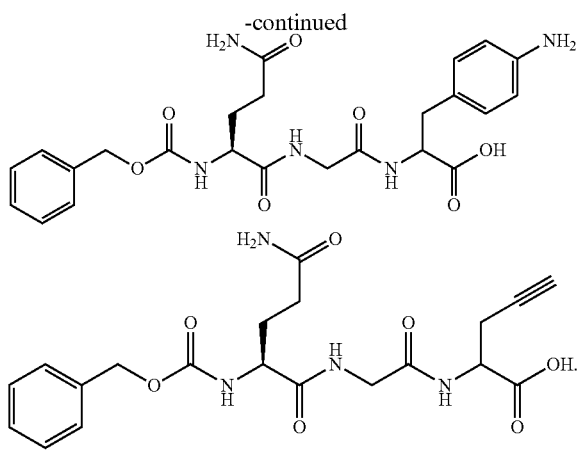

Methods of the Invention

A need for modifying the target proteins of the present invention (i.e. proteins of interest) may arise for any number of reasons, and this is also reflected in the kinds of compounds that may be selectively modified according to the methods of the present invention.

Generally, the methods of the invention comprise a transglutaminase catalysed reaction of a protein containing at least two lysines with a glutamine and glycine containing peptide of the formula R1-Gln-Gly-R2. The method consists of the following steps: (a) preparation by peptide synthesis of a compound of the formula R1-Gln-Gly-R2, and purification as known in the art; (b) mixing excess of this compound R1-Gln-Gly-R2 with a target protein containing at least one lysine, and preferably more than one lysines in an aqueous buffer, optionally containing an organic solvent, detergent or other modifier; (c) addition to this mixture of a catalytic amount of a transglutaminase, preferably microbial transglutaminase from *S. Mobarense* (the reaction is allowed to proceed for a desired amount of time); (d) a TGase inhibitor can optionally be added to the mixture; (e) the mixture is subjected to a purification process, typically comprising unit operation such as ultra- or dia-filtration and chromatography (ion exchange, size exclusion, hydrophobic interaction, etc.). In this manner a selectively modified protein is obtained. The protein is characterized by standard protein analytical methods, including chromatography, electrophoresis, peptide mapping and mass spectroscopy. Optionally, following steps (b) or (c), the modified protein can be further modified via the functional groups of R1 or R2.

Figure 4:
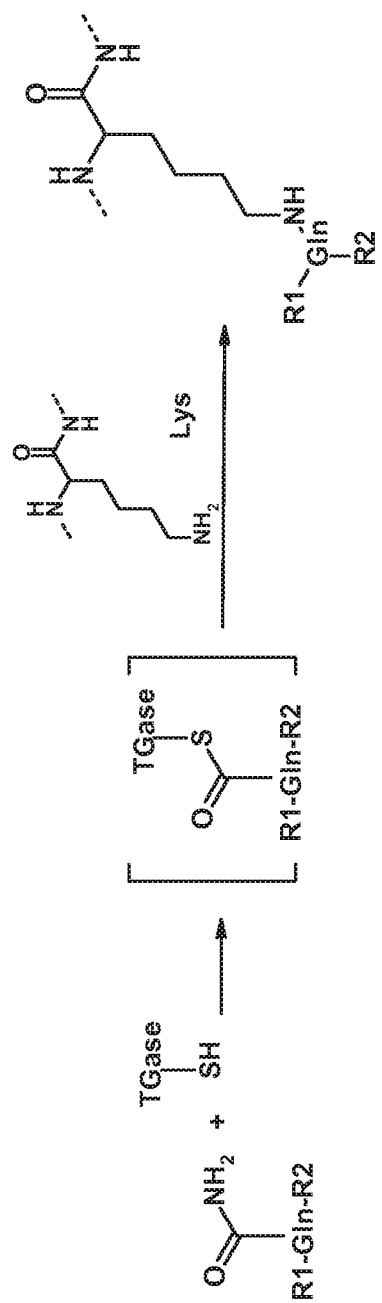
FIG. 4 depicts in detail the mechanism of the TGase-mediated transamidation.

Specifically, as part of the mechanism of the TGase-mediated transamidation, an intermolecular thioester is formed by reaction between a Cys in the active site of the TGase and the Gln-substrate (see FIG. 4). The term "transamidation" is intended to indicate a reaction where nitrogen in the side chain of glutamine is exchanged with nitrogen from another compound, in particular nitrogen from another nitrogen containing nucleophile. This intermediate may be regarded as an activated Gln-residue, the active species being a TGase-thioester, which reacts with amines, e.g. a protein lysine residue. The selectivity of the reaction is a consequence of 1) the shear steric bulk of the TGase-thioester while interacting with the Lys-bearing protein substrate, and 2) more defined non-covalent interactions between the TGase-thioester and the Lys-bearing protein substrate. An immediate consequence of this is that proteins carrying activated acyl groups, Acyl-X-protein, where is X is an atom or group that activates the acyl group towards nucleophilic attack by a protein-lysine amine, is included in the invention.

Thus, it may be desirable to modify proteins to alter the physico-chemical properties of the protein, such as e.g. to increase (or to decrease) solubility to modify the bioavailability of therapeutic proteins. In another embodiment, it may be desirable to modify the clearance rate in the body by conjugating compounds to the protein which binds to plasma proteins, such as e.g. albumin, or which increase the size of the protein to prevent or delay discharge through the kidneys. Conjugation may also alter and in particular decrease the susceptibility of a protein to hydrolysis, such as e.g. in vivo proteolysis. In another embodiment, it may be desirable to conjugate a label to facilitate analysis of the protein. Examples of such label include radioactive isotopes, fluorescent markers and enzyme substrates. In still another embodiment, a compound is conjugated to a protein to facilitate isolation of the protein. For example, a compound with a specific affinity to a particular column material may be conjugated to the protein. It may also be desirable to modify the immunogenicity of a protein, e.g. by conjugating a protein so as to hide, mask or eclipse one or more immunogenic epitopes at the protein. The term "conjugate" as a noun is intended to indicate a modified peptide, i.e. a peptide with a moiety bonded to it to modify the properties of said peptide. As a verb, the term is intended to indicate the process of bonding a moiety to a peptide to modify the properties of said peptide.

In one embodiment, the invention provides a method of improving pharmacological properties of target compounds or proteins. The improvement is with respect to the corresponding un-modified protein. Examples of such pharmacological properties include functional in vivo half-life, immunogenicity, renal filtration, protease protection and albumin binding.

The term "functional in vivo half-life" is used in its normal meaning, i.e., the time at which 50% of the biological activity of the protein or modified protein are still present in the body/target organ, or the time at which the activity of the protein or modified protein is 50% of its initial value. As an alternative to determining functional in vivo half-life, "in vivo plasma half-life" may be determined, i.e., the time at which 50% of the modified protein circulate in the plasma or bloodstream prior to being cleared. Determination of plasma half-life is often more simple than determining functional half-life and the magnitude of plasma half-life is usually a good indication of the magnitude of functional in vivo half-life. Alternative terms to plasma half-life include serum half-life, circulating half-life, circulatory half-life, serum clearance, plasma clearance, and clearance half-life.

The term "increased" as used in connection with the functional in vivo half-life or plasma half-life is used to indicate that the relevant half-life of the modified protein is statistically significantly increased relative to that of the un-modified (parent) protein, as determined under comparable conditions. For instance the relevant half-life may be increased by at least about 25%, such as by at lest about 50%, e.g., by at least about 100%, 150%, 200%, 250%, or 500%. In one embodiment, the compounds of the present invention exhibit an increase in half-life of at least about 5 h, preferably at least about 24 h, more preferably at least about 72 h, and most preferably at least about 7 days, relative to the half-life of the parent protein.

Measurement of in vivo plasma half-life can be carried out in a number of ways as described in the literature. An increase in in vivo plasma half-life may be quantified as a decrease in clearance (CL) or as an increase in mean residence time (MRT). Modified proteins of the present invention for which the CL is decreased to less than 70%, such as less than 50%, such than less than 20%, such than less than 10% of the CL of the parent protein as determined in a suitable assay is said to have an increased in vivo plasma half-life. Modified proteins of the present invention for which MRT is increased to more than 130%, such as more than 150%, such as more than 200%, such as more than 500% of the MRT of the parent protein in a suitable assay is said to have an increased in vivo plasma half-life. Clearance and mean residence time can be assessed in standard pharmacokinetic studies using suitable test animals. It is within the capabilities of a person skilled in the art to choose a suitable test animal for a given protein. Tests in human, of course, represent the ultimate test. Typically, and as an example, the mice, rats, dogs, monkeys or pigs are in injected with the compound of interest. The amount injected depends on the test animal. Subsequently, blood samples are taken over a period of one to five days as appropriate for the assessment of CL and MRT. The blood samples are conveniently analyzed by ELISA techniques.

The term "immunogenicity" of a compound refers to the ability of the compound, when administered to a human, to elicit a deleterious immune response, whether humoral, cellular, or both. In any human sub-population, there may exist individuals who exhibit sensitivity to particular administered proteins. Immunogenicity may be measured by quantifying the presence of growth hormone antibodies and/or growth hormone responsive T-cells in a sensitive individual, using conventional methods known in the art. In one embodiment, the modified protein of the present invention exhibit a decrease in immunogenicity in a sensitive individual of at least about 10%, preferably at least about 25%, more preferably at least about 40% and most preferably at least about 50%, relative to the immunogenicity for that individual of the parent protein.

The term "protease protection" or "protease protected" as used herein is intended to indicate that the modified protein of the present invention is more resistant to the plasma peptidase or proteases than is the parent protein. Protease and peptidase enzymes present in plasma are known to be involved in the degradation of circulating proteins.

Resistance of a protein to degradation by for instance dipeptidyl aminopeptidase IV (DPPIV) is determined by the following degradation assay: Aliquots of the protein (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the protein degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Proteins and their degradation products may be monitored by their absorbance at 220 nm (protein bonds) or 280 nm (aromatic amino acids), and are quantified by integration of their peak areas related to those of standards. The rate of hydrolysis of a protein by dipeptidyl aminopeptidase IV is estimated at incubation times which result in less than 10% of the protein being hydrolyzed. In one embodiment, the rate of hydrolysis of the modified protein is less than 70%, such as less than 40%, such as less than 10% of that of the parent protein.

The most abundant protein component in circulating blood of mammalian species is serum albumin, which is normally present at a concentration of approximately 3 to 4.5 grams per 100 milliliters of whole blood. Serum albumin is a blood protein of approximately 70,000 Daltons which has several important functions in the circulatory system. It functions as a transporter of a variety of organic molecules found in the blood, as the main transporter of various metabolites such as fatty acids and bilirubin through the blood, and, owing to its abundance, as an osmotic regulator of the circulating blood. Serum albumin has a half-life of more than one week, and one approach to increasing the plasma half-life of proteins has been to conjugate to the protein a group that binds to serum albumin. Albumin binding property may be determined as described in J. Med. Chem, 43, 2000, 1986-1992, which is incorporated herein by reference.

In one aspect, modified proteins of the invention may be further modified thru further derivatization of R1 and or R2. Specifically, R1 and/or R2 may comprise a chemical group suitable for further modification. Such modification can include the conjugation of a chemical group selected from the group consisting of: dendrimer, polyalkylene oxide (PAO), poly alkylene glycol (PAG), polyethylene glycol (PEG), polypropylene glycol (PPG), branched PEGS, polyvinyl alcohol (PVA), poly-carboxylate, poly-vinylpyrolidone, polyethylene-co-maleic acid anhydride, polystyrene-c-maleic acid anhydride, dextran, carboxymethyl-dextran; serum protein binding-ligands, such as compounds which bind to albumin, such as fatty acids, C5-C24 fatty acid, aliphatic diacid (e.g. C5-C24), a structure (e.g. sialic acid derivatives or mimetics) which inhibits the glycans from binding to receptors (e.g. asialoglycoprotein receptor and mannose receptor), a small organic molecule containing moieties that under physiological conditions alters charge properties, such as carboxylic acids or amines, or neutral sub-stituents that prevent glycan specific recognition such as smaller alkyl substituents (e.g., C1-C5 alkyl), a low molecular organic charged radical (e.g. C1-C25), which may contain one or more carboxylic acids, amines sulfonic, phosphonic acids, or combination thereof, a low molecular neutral hydrophilic molecule (e.g. C1-C25), such as cyclodextrin, or a polyethylene chain which may optionally branched; polyethyleneglycol with a average molecular weight of 2-40 KDa; a well defined precission polymer such as a dendrimer with an excact molecular mass ranging from 700 to 20,000 Da, or more preferably be-tween 700-10,000 Da; and a substantially non-imunogenic polypeptide such as albumin or an antibody or part of an antibody optionally containing a Fc-domain.

In one embodiment, the modified protein of the invention is PEGylated. The term "PEG" is intended to indicate polyethylene glycol of a molecular weight between approximately 100 and approximately 1,000,000 Da, including analogues thereof, wherein for instance the terminal OH-group has been replaced by an alkoxy group, such as e.g. a methoxy group, an ethoxy group or a propoxy group. In particular, the PEG wherein the terminal —OH group has been replaced by methoxy is referred to as mPEG.

The term "mPEG" (or more properly "mPEGyl") means a polydisperse or monodisperse radical of the structure:

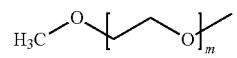

wherein m is an integer larger than 1. Thus, an mPEG wherein m is 90 has a molecular weight of 3991 Da, i.e. approx 4 kDa. Likewise, an mPEG with an average molecular weight of 20 kDa has an average m of 454. Due to the process for producing mPEG these molecules often have a distribution of molecular weights. This distribution is described by the polydispersity index.

The term "polydispersity index" as used herein means the ratio between the weight average molecular weight and the number average molecular weight, as known in the art of polymer chemistry (see e.g. "Polymer Synthesis and Characterization", J. A. Nairn, University of Utah, 2003). The polydispersity index is a number which is greater than or equal to one, and it may be estimated from Gel Permeation Chromatographic data. When the polydispersity index is 1, the product is monodisperse and is thus made up of compounds with a single molecular weight. When the polydispersity index is greater than 1 it is a measure of the polydispersity of that polymer, i.e. how broad the distribution of polymers with different molecular weights is.

The use of for example "mPEG20000" in formulas, compound names or in molecular structures indicates an mPEG residue wherein mPEG is polydisperse and has a molecular weight of approximately 20 kDa.

The polydispersity index typically increases with the molecular weight of the PEG or mPEG. When reference is made to 20 kDa PEG and in particular 20 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 30 kDa PEG and in particular 30 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 40 kDa PEG and in particular 40 kDa mPEG it is intended to indicate a compound (or in fact a mixture of compounds) with a polydisperisty index below 1.06, such as below 1.05, such as below 1.04, such as below 1.03, such as between 1.02 and 1.03.

The PEG or mPEG conjugated to modified protein through the further derivatization of the R1 and/or R2 group may be of any molecular weight. In particular the molecular weight may be between 500 and 1000,000 Da, such as between 500 and 500,000 Da, such as between 500 and 100,000 Da, such as between 500 and 60,000 Da, such as between 1000 and 40,000 Da, such as between 5000 and 40,000 Da. In particular, PEG with molecular weights of between 10,000 Da and 40,000 Da, such as between 20,000 Da and 40,000 Da, such as between 20,000 and 30,000 Da or between 30,000 and 40,000 Da may be used. Particular mentioning is made of PEG or mPEG with a molecular weight of 10,000, 20,000, 30,000 or 40,000 Da.

In one embodiment, R1 and/or R2 comprises one or more moieties that are known to bind to plasma proteins, such as e.g. albumin. The ability of a compound to bind to albumin may be determined as described in *J. Med. Chem*, 43, 2000, 1986-1992, which is incorporated herein by reference. In the present context, a compound is defined as binding to albumin if Ru/Da is above 0.05, such as above 0.10, such as above 0.12 or even above 0.15.

In another embodiment of the invention the albumin binding moiety is a protein, such as a protein comprising less than 40 amino acid residues. A number of small proteins which are albumin binding moieties are disclosed in *J. Biol Chem*. 277, 38 (2002) 35035-35043, which is incorporated herein by reference.

As discussed above, direct conjugation of modifying property groups is known (e.g. amine functionalized PEG or fatty acids conjugated to Gln containing proteins via Gln residues through the use of TGase). However, such conjugation can sometimes lack the specificity needed when derivatizing target compounds such a therapeutic proteins. Moreover, it is clear from the examples disclosed in, e.g. EP 950665, EP 785276, Sato, *Adv. Drug Delivery Rev.*, 54, 459-476, 2002 and Wada, *Biotech. Lett.*, 23, 1367-1372, 2001 that it requires a significant excess (up to 100-1000 fold) of the compound to be conjugated to the protein for the reaction to proceed. Such excess constitute a limitation to the utility of the reaction in technical or large scale. For instance, mPEG with a small poly dispersity index are very expensive, and a requirement for a large excess is in practice prohibitive. Moreover, for the conjugation of large moieties, such as e.g. PEG 10 kDa or PEG 20 k Da, excess of the reagent in the order of 100-1000 fold is not feasible due to the molecular weight of such compounds. It is also well-known that the presence of large amounts of PEG is likely to precipitate proteins, i.e. both the protein to be modified and the transglutaminase. In contrast hereto, the present method offers the advantage that the reactant which in the enzymatic step is required in large excess is a small molecule which can easily be handled even in large excess. With a proper selection of the bond to be formed in the second step no large excess is required as e.g. oxime formation takes place at almost equimolar amounts of amine- and keto-functionalities.

Target Compounds of the Invention

A target compound of the invention is preferably a protein or protein. Specifically, the protein has to be a substrate for transglutaminase according to the methods of the present invention. In one aspect, the target compound contains at least one Lys residue, and preferably at least two Lys residues. If a target compound is not a transglutaminase substrate, per se, it is possible to insert one or more Gln or Lys residues, and in particular Lys residues in the protein to make the protein a substrate for transglutaminase. In principle, such Gln or Lys residue may be inserted at any position in the sequence, however, it is preferably inserted at a position where the physiological, such as the therapeutic activity of the protein is not affected to a degree where the protein is not useful anymore, e.g. in a therapeutic intervention. Insertions of amino acid residues in proteins can be brought about by standard techniques known to persons skilled in the art, such as post-translational chemical modification or transgenetic techniques.

Any target compound or protein which are substrates to transglutaminase can be modified by the methods of the present invention, such as e.g. enzymes, protein hormones, growth factors, antibodies, cytokines, receptors, lymphokines and vaccine antigens, and particular mentioning is made of therapeutic proteins, such as insulin, glucagon like-protein 1 (GLP-1), glucagon like-protein 2 (GLP-2), growth hormone, cytokines, trefoil factor proteins (TFF), protein melanocortin receptor modifiers and factor VII compounds. Thus, target compounds of the invention include, for example, hGH, prolactin or any other cytokine; insulin, GLP1 or any other protein hormone; an antibody or fragments derived therefrom; activated factor VII, activated factor IX, factor VIII, factor XIII, or any other coagulation factor.

One such protein that would benefit from a more selective introduction of a modifying group is growth hormone. Growth hormone (GH) or somatotropin (STH) is a protein hormone which stimulates growth and cell reproduction in humans and other animals. It is a 191-amino acid, single chain polypeptide hormone which is synthesized, stored, and secreted by the somatotroph cells within the lateral wings of the anterior pituitary gland (SEQ ID NO: 4). Specifically, the genes for human growth hormone are localized in the q22-24 region of chromosome 17 and are closely related to human chorionic somatomammotropin (hCS, also known as placental lactogen) genes. GH, human chorionic somatomammotropin (hCS), and prolactin (PRL) are a group of homologous hormones with growth-promoting and lactogenic activity.

As stated above, the major isoform of the human growth hormone is a protein of 191 amino acids (SEQ ID NO:4) and a molecular weight of about 22,000 daltons. The structure includes four helices necessary for functional interaction with the GH receptor. GH is structurally and apparently evolutionarily homologous to prolactin and chorionic somatomammotropin. Despite marked structural similarities between growth hormone from different species, only human and primate growth hormones have significant effects in humans. A natural unprocessed precursor of human growth hormone comprises a 26 amino acid N-terminal signal peptide which is removed during processing. The nucleic acid and amino acid sequences for human GH precursor are set forth in SEQ ID NO: 1 and SEQ ID NO: 2, respectively. A splice variant of human GH is shown in SEQ ID NO:3. See also, Boguszewski et al., J. Clin. Endocrinol. Metab. 83(8):2878-2885 (1998).

The term "growth hormone compound" is intended to indicate human growth hormone (hGH) in which one or more amino acid residues have been deleted and/or replaced by other amino acid residues, natural or unnatural, and/or hGH comprising addition amino acid residues, natural or unnatural, and/or hGH in which at least one organic substituent is bound to one or more organic substituent. Particular mentioning is made of the 191 native amino acid sequence (somatropin) and the 192 amino acid N-terminal methionine species (somatrem).

Other examples of growth hormone compound applicable in the present invention include wherein amino acid No 172, 174, 176 and 178 as a group are replaced by one of the following groups of amino acids (R, S, F, R); (R, A, Y, R); (K, T, Y, K); (R, S, Y, R); (K, A, Y, R); (R, F, F, R); (K, Q, Y, R); (R, T, Y, H); (Q, R, Y, R); (K, K, Y, K); (R, S, F, S) or (K, S, N, R) as disclosed in WO 92/09690 (Genentech), which is incorporated herein by reference.

Other examples of growth hormone compound applicable in the present invention include hGH with the following substitutions G120R, G120K, G120Y, G120F and G120E, as disclosed in U.S. Pat. No. 6,004,931 (Genentech), which is incorporated herein by reference.

Other examples of growth hormone compound applicable in the present invention include hGH with the following set of substitutions R167N, D171S, E174S, F176Y and I179T; R176E, D171S, E174S and F176Y; F10A, M14W, H18D and H21N; F10A, M14W, H18D, H21N, R167N, D171S, E174S, F176Y, I179T; F10A, M14W, H18D, H21N, R167N, D171A, E174S, F176Y, I179T; F10H, M14G, H18N and H21N; F10A, M14W, H18D, H21N, R167N, D171A, T175T and I179T; and F10I, M14Q, H18E, R167N, D171S and I179T, as disclosed in U.S. Pat. No. 6,143,523 (Genentech), which is incorporated herein by reference.

Other examples of growth hormone compound applicable in the present invention include hGH with the following set of substitutions H18A, Q22A, F25A, D26A, Q29A, E65A, K168A, E174A and G120K as disclosed in U.S. Pat. No. 6,136,536 (Genentech), which is incorporated herein by reference.

Other examples of growth hormone compound applicable in the present invention include hGH with the following set of substitutions H18D, H21N, R167N, K168A, D171S, K172R, E174S, I179T and wherein G120 is further substituted with either R, K, W, Y, F or E, as disclosed in U.S. Pat. No. 6,057,292 (Genentech), which is incorporated herein by reference.

Other examples of growth hormone compound applicable in the present invention include hGH with the following set of substitutions H18D, H21N, R167N, K168A, D171S, K172R, E174S and I179T, as disclosed in U.S. Pat. No. 5,849,535 (Genentech), which is incorporated herein by reference.

Other examples of growth hormone compound applicable in the present invention include hGH with the following set of substitutions H18D, H21D, R167N, K168A, D171S, K172R, E174S and I179T; and H18A, Q22A, F25A, D26A, Q29A, E65A, K168A and E174A, as disclosed in WO 97/11178 (Genentech), which is incorporated herein by reference.

Other examples of growth hormone compound applicable in the present invention include hGH with the following set of substitutions K168A and E174A; R178N and I179M; K172A and F176A; and H54F, S56E, L58I, E62S, D63N and Q66E as disclosed in WO 90/04788 (Genentech), which is incorporated herein by reference.

When the methods of the present invention are performed on a target compound comprising hGH, the reaction leads to selective modification of at least one Lys selected from Lys64, Lys67, Lys96, Lys14I, Lys166, Lys171, Lys184, Lys194 and Lys198 of SEQ ID NO: 2. In a preferred embodiment, primarily one single lysine, Lys 171 of SEQ ID NO: 2 (corresponding to Lys 145 of SEQ ID NO: 4) is modified. In another embodiment, at least two Lys are modified.

In yet another embodiment, Lys171 is modified with one property modifying group and a secondary Lys is modified with a second, different property modifying group, as disclosed herein.

Another protein which would benefit from the methods of the present invention is insulin and in particular, human insulin. In the present context the term "human insulin" refers to naturally produced insulin or recombinantly produced insulin. Recombinant human insulin may be produced in any suitable host cell, for example the host cells may be bacterial, fungal (including yeast), insect, animal or plant cells. Many insulin compounds have been disclosed in the literature, and they too are particular useful in the methods of the present invention. By "insulin compound" (and related expressions) is meant human insulin in which one or more amino acids have been deleted and/or replaced by other amino acids, including non-codeable amino acids, and/or human insulin comprising additional amino acids, i.e. more than 51 amino acids, and/or human insulin in which at least one organic substituent is bound to one or more of the amino acids.

The following patent documents are mentioned as disclosures of insulin compounds particularly applicable in the methods provided by the present invention.

WO 97/31022 (Novo Nordisk), which is incorporated herein by reference, discloses insulin compounds with a protracted activity profile wherein the amino group of the N-terminal amino acid of the B-chain and/or the ε-amino group of $Lys^{B29}$ has a carboxylic acid containing lipophilic substituent. Particular mentioning is made of $N^{\epsilon B29}$—(CO—$(CH_2)_{14}$—COOH) human insulin; $N^{\epsilon B29}$—(CO—$(CH_2)_{16}$—COOH) human insulin; $N^{\epsilon B29}$—(CO—$(CH_2)_{18}$—COOH) human insulin; $N^{\epsilon B29}$—(CO—$(CH_2)_{20}$—COOH); $N^{\epsilon B29}$—(CO—$(CH_2)_{22}$—COOH) human insulin; $N^{\epsilon B29}$—(CO—$(CH_2)_{14}$—COOH) $Asp^{B28}$-human insulin; $N^{\epsilon B29}$—(CO—$(CH_2)_{16}$—COOH) $Asp^{B28}$-human insulin; $N^{\epsilon B29}$—(CO—$(CH_2)_{18}$—COOH) $Asp^{B28}$-human insulin; $N^{\epsilon B29}$—(CO—$(CH_2)_{20}$—COOH) $Asp^{B28}$-human insulin; $N^{\epsilon B29}$—(CO—$(CH_2)_{22}$—COOH) $Asp^{B28}$-human insulin; $N^{\epsilon B30}$—(CO—$(CH_2)_{14}$—COOH) $Thr^{B29}Lys^{B30}$-human insulin; $N^{\epsilon B30}$—(CO—$(CH_2)_{16}$—COOH) $Thr^{B29}Lys^{B30}$-human insulin; $N^{\epsilon B30}$—(CO—$(CH_2)_{18}$—COOH) $Thr^{B29}Lys^{B30}$-human insulin; $N^{\epsilon B30}$—(CO—$(CH_2)_{20}$—COOH) $Thr^{B29}Lys^{B30}$-human insulin; $N^{\epsilon B30}$—(CO—(CH$_2$)$_{22}$—COOH) Thr$^{B29}$Lys$^{B30}$-human insulin; $N^{\epsilon B28}$—(CO—(CH$_2$)$_{14}$—COOH) Lys$^{B28}$Pro$^{B29}$-human insulin; $N^{\epsilon B28}$—(CO—(CH$_2$)$_{16}$—COOH) Lys$^{B28}$Pro$^{B29}$-human insulin; $N^{\epsilon B28}$—(CO—(CH$_2$)$_{18}$—COOH) Lys$^{B28}$Pro$^{B29}$-human insulin; $N^{\epsilon B28}$—(CO—(CH$_2$)$_{20}$—COOH) Lys$^{B28}$Pro$^{B29}$-human insulin; $N^{\epsilon B28}$—(CO—(CH$_2$)$_{22}$—COOH) Lys$^{B28}$Pro$^{B29}$-human insulin; $N^{\epsilon B29}$—(CO—(CH$_2$)$_{14}$—COOH) desB30 human insulin; $N^{\epsilon B29}$—(CO—(CH$_2$)$_{16}$—COOH) desB30 human insulin; $N^{\epsilon B29}$—(CO—(CH$_2$)$_{18}$—COOH) desB30 human insulin; $N^{\epsilon B29}$—(CO—(CH$_2$)$_{20}$—COOH) desB30 human insulin; and $N^{\epsilon B29}$—(CO—(CH$_2$)$_{22}$COOH) desB30 human insulin.

WO 96/29344 (Novo Nordisk), which is incorporated herein by reference, discloses insulin compounds with a protracted activity profile wherein either the amino group of the N-terminal amino acid of the B-chain has a lipophilic substituent comprising from 12 to 40 carbon atoms attached, or wherein the carboxylic acid group of the C-terminal amino acid of the B-chain has a lipophilic substituent comprising from 12 to 40 carbon atoms attached.

WO 95/07931 (Novo Nordisk), which is incorporated herein by reference, discloses insulin compounds with a protracted activity profile, wherein the ε-amino group of Lys$^{B29}$ has a lipophilic substituent. Particular mentioning is made of $N^{\epsilon B29}$-tridecanoyl des(B30) human insulin, $N^{\epsilon B29}$-tetradecanoyl des(B30) human insulin, $N^{\epsilon B29}$-decanoyl des(B30) human insulin, $N^{\epsilon B29}$-dodecanoyl des(B30) human insulin, $N^{\epsilon B29}$-tridecanoyl Gly$^{A21}$ des(B30) human insulin, $N^{\epsilon B29}$-tetradecanoyl Gly$^{A21}$ des(B30) human insulin, $N^{\epsilon B29}$-decanoyl Gly$^{A21}$ des(B30) human insulin, $N^{\epsilon B29}$-dodecanoyl Gly$^{A21}$ des(B30) human insulin, $N^{\epsilon B29}$-tridecanoyl Gly$^{A21}$ Gln$^{B3}$ des(B30) human insulin, $N^{\epsilon B29}$-tetradecanoyl Gly$^{A21}$ Gln$^{B3}$ des(B30) human insulin, $N^{\epsilon B29}$-decanoyl Gly$^{A21}$ Gln$^{B3}$ des(B30) human insulin, $N^{\epsilon B29}$-dodecanoyl Gly$^{A21}$ Gln$^{B3}$ des(B30) human insulin, $N^{\epsilon B29}$-tridecanoyl Ala$^{A21}$ des(B30) human insulin, $N^{\epsilon B29}$-tetradecanoyl Ala$^{A21}$ des(B30) human insulin, $N^{\epsilon B29}$-decanoyl Ala$^{A21}$ des(B30) human insulin, $N^{\epsilon B29}$-dodecanoyl Ala$^{A21}$ des(B30) human insulin, $N^{\epsilon B29}$-tridecanoyl Ala$^{A21}$ Gln$^{B3}$ des(B30) human insulin, $N^{\epsilon B29}$-tetradecanoyl Ala$^{A21}$ Gln$^{B3}$ des(B30) human insulin, $N^{\epsilon B29}$-decanoyl Ala$^{A21}$ Gln$^{B3}$ des(B30) human insulin, $N^{\epsilon B29}$-dodecanoyl Ala$^{A21}$ Gln$^{B3}$ des(B30) human insulin, $N^{\epsilon B29}$-tridecanoyl Gln$^{B3}$ des(B30) human insulin, $N^{\epsilon B29}$-tetradecanoyl Gln$^{B3}$ des(B30) human insulin, $N^{\epsilon B29}$-decanoyl Gln$^{B3}$ des(B30) human insulin, $N^{\epsilon B29}$-dodecanoyl Gln$^{B3}$ des(B30) human insulin, $N^{\epsilon B29}$-tridecanoyl Gly$^{A21}$ human insulin, $N^{\epsilon B29}$-tetradecanoyl Gly$^{A21}$ human insulin, $N^{\epsilon B29}$-decanoyl Gly$^{A21}$ human insulin, $N^{\epsilon B29}$-dodecanoyl Gly$^{A21}$ human insulin, $N^{\epsilon B29}$-tridecanoyl Gly$^{A21}$ Gln$^{B3}$ human insulin, $N^{\epsilon B29}$-tetradecanoyl Gly$^{A21}$ Gln$^{B3}$ human insulin, $N^{\epsilon B29}$-decanoyl Gly$^{A21}$ Gln$^{B3}$ human insulin, $N^{\epsilon B29}$-dodecanoyl Gly$^{A21}$ Gln$^{B3}$ human insulin, $N^{\epsilon B29}$-tridecanoyl Ala$^{A21}$ human insulin, $N^{\epsilon B29}$-tetradecanoyl Ala$^{A21}$ human insulin, $N^{\epsilon B29}$-decanoyl Ala$^{A21}$ human insulin, $N^{\epsilon B29}$-dodecanoyl Ala$^{A21}$ human insulin, $N^{\epsilon B29}$-tridecanoyl Ala$^{A21}$ Gln$^{B3}$ human insulin, $N^{\epsilon B29}$-tetradecanoyl Ala$^{A21}$ Gln$^{B3}$ human insulin, $N^{\epsilon B29}$-decanoyl Ala$^{A21}$ Gln$^{B3}$ human insulin, $N^{\epsilon B29}$-dodecanoyl Ala$^{A21}$ Gln$^{B3}$ human insulin, $N^{\epsilon B29}$-tridecanoyl Gln$^{B3}$ human insulin, $N^{\epsilon B29}$-tetradecanoyl Gln$^{B3}$ human insulin, $N^{\epsilon B29}$-decanoyl Gln$^{B3}$ human insulin, $N^{\epsilon B29}$-dodecanoyl Gln$^{B3}$ human insulin, $N^{\epsilon B29}$-tridecanoyl Glu$^{B30}$ human insulin, $N^{\epsilon B29}$-tetradecanoyl Glu$^{B30}$ human insulin, $N^{\epsilon B29}$-decanoyl Glu$^{B30}$ human insulin, $N^{\epsilon B29}$-dodecanoyl Glu$^{B30}$ human insulin, $N^{\epsilon B29}$-tridecanoyl Gly$^{A21}$ Glu$^{B30}$ human insulin, $N^{\epsilon B29}$-tetradecanoyl Gly$^{A21}$ Glu$^{B30}$ human insulin, $N^{\epsilon B29}$-decanoyl Gly$^{A21}$ Glu$^{B30}$ human insulin, $N^{\epsilon B29}$-dodecanoyl Gly$^{A21}$ Glu$^{B30}$ human insulin, $N^{\epsilon B29}$-tridecanoyl Gly$^{A21}$ Gln$^{B3}$ Glu$^{B30}$ human insulin, $N^{\epsilon B29}$-tetradecanoyl Gly$^{A21}$ Gln$^{B3}$ Glu$^{B30}$ human insulin, $N^{\epsilon B29}$-decanoyl Gly$^{A21}$ Gln$^{B3}$ Glu$^{B30}$ human insulin, $N^{\epsilon B29}$-dodecanoyl Gly$^{A21}$ Gln$^{B3}$ Glu$^{B30}$ human insulin, $N^{\epsilon B29}$-tridecanoyl Ala$^{A21}$ Glu$^{B30}$ human insulin, $N^{\epsilon B29}$-tetradecanoyl Ala$^{A21}$ Glu$^{B30}$ human insulin, $N^{\epsilon B29}$-decanoyl Ala$^{A21}$ Glu$^{B30}$ human insulin, $N^{\epsilon B29}$-dodecanoyl Ala$^{A21}$ Glu$^{B30}$ human insulin, $N^{\epsilon B29}$-tridecanoyl Ala$^{A21}$ Gln$^{B3}$ Glu$^{B30}$ human insulin, $N^{\epsilon B29}$-tetradecanoyl Ala$^{A21}$ Gln$^{B3}$ Glu$^{B30}$ human insulin, $N^{\epsilon B29}$-decanoyl Ala$^{A21}$ Gln$^{B3}$ Glu$^{B30}$ human insulin, $N^{\epsilon B29}$-dodecanoyl Ala$^{A21}$ Gln$^{B3}$ Glu$^{B30}$ human insulin, $N^{\epsilon B29}$-tridecanoyl Gln$^{B3}$ Glu$^{B30}$ human insulin, $N^{\epsilon B29}$-tetradecanoyl Gln$^{B3}$ Glu$^{B30}$ human insulin, $N^{\epsilon B29}$-decanoyl Gln$^{B3}$ Glu$^{B30}$ human insulin and $N^{\epsilon B29}$-dodecanoyl Gln$^{B3}$ Glu$^{B30}$ human insulin.

WO 97/02043 (Novo Nordisk), which is incorporated herein by reference discloses hormonally inactive insulin compounds which are useful in insulin prophylaxis, and in particular such analogues of human insulin are selected from amongst desA1 human insulin; des(A1-A2) human insulin; des(A1-A3) human insulin; desA21 human insulin; des(B1-B5) human insulin; des(B1-B6) human insulin; des(B23-B30) human insulin; des(B24-B30) human insulin; des(B25-B30) human insulin; Gly$^{A2}$ human insulin; Ala$^{A2}$ human insulin; Nle$^{A2}$ human insulin; Thr$^{A2}$ human insulin; Pro$^{A2}$ human insulin; D-allo Ile$^{A2}$ human insulin; Nva$^{A3}$ human insulin; Nle$^{A3}$ human insulin; Leu$^{A3}$ human insulin; Val$^{A2}$, Ile$^{A3}$ human insulin; Abu$^{A2}$,Abu$^{A3}$ human insulin; Gly$^{A2}$, Gly$^{A3}$ human insulin; D-Cys$^{A6}$ human insulin; D-Cys$^{A6}$,D-Cys$^{A11}$ human insulin; Ser$^{A6}$,Ser$^{A11}$,des(A8-A10) human insulin; D-Cys$^{A7}$ human insulin; D-Cys$^{A11}$ human insulin; Leu$^{A19}$ human insulin; Gly$^{B6}$ human insulin; Glu$^{B12}$ human insulin; Asn$^{B12}$ human insulin; Phe$^{B12}$ human insulin; D-Ala$^{B12}$ human insulin; and Asp$^{B25}$ human insulin are applicable in the methods of the present invention.

WO 92/15611 (Novo nordisk), which is incorporated herein by reference, discloses analogues of human insulin with a fast association rate constants in the insulin receptor binding process and characterized by comprising a tyrosine in position A13 and/or a phenylalanine, tryptophane or tyrosine in position B17. In particular, such analogues are selected from amongst Tyr$^{A13}$ human insulin, Phe$^{B17}$ human insulin, Trp$^{B17}$ human insulin, Tyr$^{B17}$ human insulin, Tyr$^{A13}$,Phe$^{B17}$ human insulin, Tyr$^{A13}$,Trp$^{B17}$ human insulin, Tyr$^{A13}$,Tyr$^{B17}$ human insulin, Phe$^{A13}$,Phe$^{B17}$ human insulin, Phe$^{A13}$,Trp$^{B17}$ human insulin, Phe$^{A13}$,Tyr$^{B17}$ human insulin, Trp$^{A13}$,Phe$^{B17}$ human insulin, Trp$^{A13}$,Trp$^{B17}$ human insulin and Trp$^{A13}$, Tyr$^{B17}$ human insulin.

WO 92/00322 (Novo Nordisk), which is incorporated herein by reference, discloses analogues of human insulin which are capable of being targeted to specific tissues, and which are characterized by having in the A13 position and/or in the B17 position in the insulin molecule a naturally occurring amino acid residue different from leucine and/or by having in the B18 position in the insulin molecule a naturally occurring amino acid residue different from valine. In particular, such analogues are selected from amongst Ala$^{B17}$ human insulin, Ala$^{B18}$ human insulin, Asn$^{A13}$ human insulin, Asn$^{A13}$,Ala$^{B17}$ human insulin, Asn$^{A13}$,Asp$^{B17}$ human insulin, Asn$^{A13}$,Glu$^{B17}$ human insulin, Asn$^{B18}$ human insulin, Asp$^{A13}$ human insulin, Asp$^{A13}$,Ala$^{B17}$ human insulin, Asp$^{A13}$,Asp$^{B17}$ human insulin, Asp$^{A13}$,Glu$^{B17}$ human insulin, Asp$^{B18}$ human insulin, Gln$^{A13}$ human insulin, Gln$^{A13}$,Ala$^{B17}$ human insulin, Gln$^{A13}$,Asp$^{B17}$ human insulin, Gln$^{B18}$ human insulin, Glu$^{A13}$ human insulin, Glu$^{A13}$,Ala$^{B17}$ human insulin, Glu$^{A13}$,Asp$^{B17}$ human insulin, Glu$^{A13}$,Glu$^{B17}$ human insulin, Glu$^{B18}$ human insulin, Gly$^{A13}$ human insulin, Gly$^{A13}$,Ala$^{B17}$ human insulin, Gly$^{A13}$,Asn$^{B17}$ human insulin, Gly$^{A13}$,Asp$^{B17}$ human insulin, Gly$^{A13}$,Glu$^{B17}$ human insulin, Gly$^{B18}$ human insulin, Ser$^{A13}$ human insulin, Ser$^{A13}$,Gln$^{A17}$,Glu$^{B10}$,Gln$^{B17}$-des(Thr$^{B30}$) human insulin, Ser$^{A13}$,Ala$^{B17}$ human insulin, Ser$^{A13}$,Asn$^{B17}$ human insulin, Ser$^{A13}$,Asp$^{B17}$ human insulin, Ser$^{A13}$,Gln$^{B17}$ human insulin, Ser$^{A13}$,Glu$^{B17}$ human insulin, Ser$^{A13}$,Thr$^{B17}$ human insulin, Ser$^{A14}$,Asp$^{B17}$ human insulin, Ser$^{B18}$ human insulin, Thr$^{A13}$ human insulin or Thr$^{B18}$ human insulin.

WO 90/01038 (Novo Nordisk), which is incorporated herein by reference, discloses analogues of human insulin with high biological activity and characterized by having Phe$^{B25}$ substituted by His or Tyr, by having substitutions in one or more of positions A4, A8, A17, A21, B9, B10, B12, B13, B21, B26, B27, B28 and B30, and by having the amino acid residue at position B30 optionally absent. In particular, such analogues are selected from amongst Tyr$^{B25}$ human insulin, Tyr$^{B25}$,Asp$^{B28}$ human insulin, His$^{B25}$ human insulin, His$^{B25}$,Asp$^{B28}$ human insulin, Tyr$^{B25}$ human insulin-B30-amide and His$^{B25}$ human insulin-B30-amide.

WO 86/05496 (Nordisk Gentofte) discloses analogues of human insulin with a protracted action and characterized by having a blocked B30 carboxylic group, and by having one to four blocked carboxylic groups in the amino acid residues at positions A4, A17, A21, B13 and B21. In particular, such analogues are selected from amongst insulin-B30-octyl ester, insulin-B30-dodecyl amide, insulin-B30-hexadecyl amide, insulin-(B21,B30)-dimethyl ester, insulin-(B17,B30)-dimethyl ester, insulin-(A4,B30) diamide, insulin-A17amide-B30-octyl ester, insulin-(A4,B13)-diamide-B30-hexylamide, insulin-(A4,A17,B21,B30)-tetraamide, insulin-(A17,B30)-diamide, A4-Ala-insulin-B30-amide and B30-Leu-insulin-(A4,B30)-diamide.

WO 86/05497 (Nordisk Gentofte), which is incorporated herein by reference, discloses insulin compounds in which one or more of the four amino acid residues in positions A4, A17, B13 and B21 comprises an uncharged side chain. Particular mentioning is made of human insulin A17-Gln, human insulin A4-Gln, porcine insulin B21-Gln, human insulin B13-Gln, human insulin (A17,B21)-Gln, human insulin A4-Ala, human insulin B21-Thr, human insulin B13-Val, human insulin-Thr-A17-Gln, human insulin B21-methyl ester and human insulin A17-methyl ester.

WO 92/00321 (Novo Nordisk), which is incorporated herein by reference, discloses insulin compounds with prolonged activity wherein a positive charge in the N-terminal end of the B-chain has been introduced. Particular mentioning is made of Arg$^{B5}$,Ser$^{A21}$,Thr$^{B30}$-NH$_2$ human insulin, Arg$^{B5}$,Pro$^{B6}$,Ser$^{A21}$,Thr$^{B30}$-NH$_2$ human insulin, Arg$^{B5}$,Gly$^{A21}$,Thr$^{B30}$-NH$_2$ human insulin, Arg$^{B5}$,Pro$^{B6}$,Gly$^{A21}$,Thr$^{B30}$-NH$_2$ human insulin, Arg$^{B2}$,Ser$^{A21}$,Thr$^{B30}$-NH$_2$ human insulin, Arg$^{B2}$,Pro$^{B3}$,Ser$^{A21}$,Thr$^{B30}$-NH$_2$ human insulin, Arg$^{B2}$,Gly$^{A21}$,Thr$^{B30}$-NH$_2$ human insulin, Arg$^{B2}$,Pro$^{B3}$,Gly$^{A21}$,Thr$^{B30}$-NH$_2$ human insulin, Arg$^{B2}$,Arg$^{B3}$,Ser$^{A21}$,Thr$^{B30}$-NH$_2$ human insulin, Arg$^{B2}$,Arg$^{B3}$,Ser$^{A21}$ human insulin, Arg$^{B4}$,Pro$^{B5}$,Ser$^{A21}$,Thr$^{B30}$-NH$_2$ human insulin, Arg$^{B4}$,Arg$^{B5}$,Pro$^{B6}$,Gly$^{A21}$,Thr$^{B30}$ human insulin, Arg$^{B3}$,Gly$^{A21}$,Thr$^{B30}$-NH$_2$ human insulin, Arg$^{B3}$,Ser$^{A21}$,Thr$^{B30}$-NH$_2$ human insulin, Arg$^{B4}$,Gly$^{A21}$,Thr$^{B30}$-NH$_2$ human insulin, Arg$^{B4}$,Ser$^{A21}$,Thr$^{B30}$-NH$_2$ human insulin and Arg$^{B1}$,Pro$^{B2}$,Gly$^{A21}$,Thr$^{B30}$-NH$_2$ human insulin.

WO 90/07522 (Novo Nordisk), which is incorporated herein by reference, discloses insulin compounds exhibiting a low ability to associate in solution wherein there is a positively charged amino acid residue, i.e. Lys or Arg in the position B28. Particular mentioning is made of des[Phe$^{B25}$]-human insulin, des[Tyr$^{B26}$]-human insulin, des[Thr$^{B27}$]-human insulin, des[Pro$^{B28}$]-human insulin, des[Phe$^{B25}$]-porcine insulin, des[Pro$^{B28}$]-porcine insulin, des[Pro$^{B28}$]-rabbit insulin, des[Phe$^{B25}$],des[Thr$^{B30}$]-human insulin, des[Tyr$^{B26}$],des[Thr$^{B30}$]-human insulin, [Ser$^{A21}$]-des[Pro$^{B28}$]-human insulin, [Gly$^{A21}$]-des[Pro$^{B28}$]-human insulin, [Gly$^{A21}$]-des[Phe$^{B25}$]-human insulin, [Asp$^{A21}$]-des[Phe$^{B25}$]-human insulin, [His$^{B25}$]-des[Tyr$^{B26}$],des[Thr$^{B30}$]-human insulin, [Asn$^{B25}$]-des[Tyr$^{B26}$],des[Thr$^{B30}$]-human insulin, [Asp$^{A21}$]-des[Phe$^{B25}$],des[Thr$^{B30}$]-human insulin, [Asp$^{B28}$]-des[Phe$^{B25}$]-human insulin, [Asp$^{B3}$]-des[Phe$^{B25}$]-human insulin, [Lys$^{B28}$]-human insulin, [Lys$^{B28}$,Thr$^{B29}$]-human insulin and [Arg$^{B28}$]-des[Lys$^{B29}$]-human insulin.

WO 90/11290 (Novo Nordisk), which is incorporated herein by reference discloses insulin compounds with a prolonged activity. Particular mentioning is made of [Arg$^{A0}$]-human insulin-(B30-amide), [Arg$^{A0}$,Gln$^{B13}$]-human insulin-(B30-amide), [Arg$^{A0}$,Gln$^{A4}$,Asp$^{A21}$]-human insulin-(B30-amide), [Arg$^{A0}$,Ser$^{A21}$]-human insulin-(B30-amide) and [Arg$^{A0}$,Arg$^{B27}$]-des[Thr$^{B30}$]-human insulin.

WO 90/10645 (Novo Nordisk), which is incorporated herein by reference discloses glycosylated insulins. Particular mentioning is made of Phe(B1) glucose human insulin, Phe(B1) mannose human insulin, Gly(A1) mannose human insulin, Lys(B29) mannose human insulin, Phe(B1) galactose human insulin, Gly(A1) galactose human insulin, Lys(B29) galactose human insulin, Phe(B1) maltose human insulin, Phe(B1) lactose human insulin, Gly(A1) glucose human insulin, Gly(A1) maltose human insulin, Gly(A1) lactose human insulin, Lys(B29) glucose human insulin, Lys(B29) maltose human insulin, Lys(B29) lactose human insulin, Gly(A1),Phe(B1) diglucose human insulin, Gly(A1),Lys(B29) diglucose human insulin, Phe(B1),Lys(B29) diglucose human insulin, Phe(B1) isomaltose human insulin, Gly(A1) isomaltose human insulin, Lys(B29) isomaltose human insulin, Phe(B1) maltotriose human insulin, Gly(A1) maltotriose human insulin, Lys(B29) maltotriose human insulin, Gly(A1),Phe(B1) dimaltose human insulin, Gly(A1),Lys(B29) dimaltose human insulin, Phe(B1),Lys(B29) dimaltose human insulin, Gly(A1),Phe(B1) dilactose human insulin, Gly(A1),Lys(B29) dilactose human insulin, Phe(B1),Lys(B29) dilactose human insulin, Gly(A1),Phe(B1) dimaltotriose human insulin, Gly(A1),Lys(B29) dimaltotriose human insulin, Phe(B1),Lys(B29) dimaltotriose human insulin, Phe(B1),Gly(A1) dimannose human insulin, Phe(B1),Lys(B29) dimannose human insulin, Gly(A1),Lys(B29) dimannose human insulin, Phe(B1),Gly(A1) digalactose human insulin, Phe(B1),Lys(B29) digalactose human insulin, Gly(A1),Lys(B29) digalactose human insulin, Phe(B1),Gly(A1) diisomaltose human insulin, Phe(B1),Lys(B29) diisomaltose human insulin, Gly(A1),Lys(B29) diisomaltose human insulin, Phe (B1) glucose [Asp$^{B10}$] human insulin and Gly(A1),Phe(B1) diglucose [Asp$^{B10}$] human insulin.

WO 88/065999 (Novo Nordisk), which is incorporated herein by reference, discloses stabilized insulin compounds, wherein Ans$^{21A}$ has been substituted with other amino acid residues. Particular mentioning is made of Gly$^{A21}$ human insulin, Ala$^{A21}$ human insulin, Ser$^{A21}$ human insulin, Thr$^{A21}$ human insulin and hSer$^{A21}$ human insulin.

EP 254516 (Novo Nordisk), which is incorporated herein by reference, discloses insulin compounds with a prolonged action, wherein basic amino acid residues have been substituted by neutral amino acid residues. Particular mentioning is made of: Gly$^{A21}$,Lys$^{B27}$,Thr$^{B30}$-NH$_2$ human insulin, Ser$^{A21}$, Lys$^{B27}$,Thr$^{B30}$-NH$_2$ human insulin, Thr$^{A21}$,Lys$^{B27}$,Thr$^{B30}$-NH$_2$ human insulin, Ala$^{A21}$,Lys$^{B27}$,Thr$^{B30}$-NH$_2$ human insulin, His$^{A21}$,Lys$^{B27}$,Thr$^{B30}$-NH$_2$ human insulin, Asp$^{B21}$,Lys$^{B27}$,Thr$^{B30}$-NN$_2$ human Insulin, Gly$^{A21}$,Arg$^{B21}$,Thr$^{B30}$-NH$_2$ human insulin Ser$^{A21}$,Arg$^{B27}$,Thr$^{B30}$-NH$_2$ human insulin, Thr$^{A21}$,Arg$^{B27}$,Thr$^{B30}$-NH$_2$ human insulin, Ala$^{B21}$, Arg$^{B27}$,Thr$^{B30}$-NH$_2$ human insulin, His$^{A21}$,Arg$^{B27}$,Thr$^{B30}$-NH$_2$ human insulin, Asp$^{B21}$,Arg$^{B27}$,Thr$^{B30}$-NH$_2$ human insulin, Gln$^{B13}$,Gly$^{A21}$,Arg$^{B27}$,Thr$^{B30}$-NH$_2$ human insulin, Gln$^{B13}$,Ser$^{A21}$,Thr$^{B30}$-NH$_2$ human insulin, Gln$^{B13}$,Ser$^{A21}$,Arg$^{B27}$,Thr$^{B30}$-NH$_2$ human insulin, Gln$^{B13}$,Thr$^{A21}$,Arg$^{B27}$,Thr$^{B30}$-NH$_2$ human insulin, Gln$^{B13}$,Ala$^{A21}$,Arg$^{B27}$,Thr$^{B30}$-NH$_2$ human insulin, Gln$^{B13}$,His$^{A21}$,Arg$^{B27}$,Thr$^{B30}$-NH$_2$ human insulin, Gln$^{B13}$,Asp$^{A21}$,Arg$^{B27}$,Thr$^{B30}$-NH$_2$ human insulin, Gln$^{B13}$,Gly$^{A21}$,Lys$^{B27}$,Thr$^{B30}$-NH$_2$ human insulin, Gln$^{B13}$,Ser$^{A21}$,Lys$^{B27}$,Thr$^{B30}$-NH$_2$ human insulin, Gln$^{B13}$,Thr$^{A21}$,Lys$^{B27}$,Thr$^{B30}$-NH$_2$ human insulin, Gln$^{B13}$,Ala$^{A21}$,Lys$^{B27}$,Thr$^{B30}$-NH$_2$ human insulin, Gln$^{B13}$,His$^{A21}$,Lys$^{B27}$,Thr$^{B30}$-NH$_2$ human insulin, Gln$^{B13}$,Asp$^{A21}$,Lys$^{B27}$,Thr$^{B30}$-NH$_2$ human insulin, Asn$^{A21}$,Lys$^{B27}$ human insulin, Ser$^{A21}$,Lys$^{B27}$ human insulin, Thr$^{A21}$,Lys$^{B27}$, human insulin, Ala$^{A21}$,Lys$^{B27}$ human insulin, His$^{A21}$,Lys$^{B27}$ human insulin, Asp$^{A21}$,Lys$^{B27}$ human insulin, Gly$^{A21}$,Lys$^{B27}$ human insulin, Asn$^{A21}$,Arg$^{B27}$ human insulin, Ser$^{A21}$,Arg$^{B27}$ human insulin, Thr$^{A21}$,Arg$^{B27}$ human insulin, Ala$^{A21}$,Arg$^{B27}$ human insulin, His$^{A21}$,Arg$^{B27}$ human insulin, Asp$^{A21}$,Arg$^{B27}$ human insulin, Gly$^{A21}$,Arg$^{B27}$ human insulin, Gln$^{A17}$,Asn$^{A21}$,Arg$^{B27}$human insulin, Gln$^{A17}$,Ser$^{A21}$,Arg$^{B27}$human insulin, Gln$^{A17}$,Thr$^{A21}$,Arg$^{B27}$human insulin, Gln$^{A17}$,Ala$^{A21}$,Arg$^{B27}$human insulin, Gln$^{A17}$,His$^{A21}$,Arg$^{B27}$human insulin, Gln$^{A17}$,Asp$^{A21}$,Arg$^{B27}$human insulin, Gln$^{A17}$,Gly$^{A21}$,Arg$^{B27}$human insulin, Gln$^{A17}$,Asn$^{A21}$,Gln$^{B13}$human insulin, Gln$^{A17}$,Ser$^{A21}$,Gln$^{B13}$human insulin, Gln$^{A17}$,Thr$^{A21}$,Gln$^{B13}$human insulin, Gln$^{A17}$,Ala$^{A21}$,Gln$^{B13}$human insulin, Gln$^{A17}$,His$^{A21}$,Gln$^{B13}$human insulin, Gln$^{A17}$,Asp$^{A21}$,Gln$^{B13}$human insulin, Gln$^{A17}$,Gly$^{A21}$,Gln$^{B13}$human insulin, Arg$^{A27}$,Asn$^{A21}$,Gln$^{B13}$human insulin, Arg$^{A27}$,Ser$^{A21}$,Gln$^{B13}$human insulin, Arg$^{A27}$,Thr$^{A21}$,Gln$^{B13}$human insulin, Arg$^{A27}$,Ala$^{A21}$,Gln$^{B13}$human insulin, Arg$^{A27}$,His$^{A21}$,Gln$^{B13}$human insulin, Arg$^{A27}$,Asp$^{A21}$Gln$^{B13}$human insulin, Arg$^{A27}$,Gly$^{A21}$,Gln$^{B13}$human insulin, Gln$^{A17}$,Asn$^{A21}$,Lys$^{B27}$human insulin, Gln$^{A17}$,Ser$^{A21}$,Lys$^{B27}$human insulin, Gln$^{A17}$,Thr$^{A21}$,Lys$^{B27}$human insulin, Gln$^{A17}$,Ala$^{A21}$,Lys$^{B27}$human insulin, Gln$^{A17}$,His$^{A21}$,Lys$^{B27}$human insulin, Gln$^{A17}$,Asp$^{A21}$,Lys$^{B27}$human insulin, Gln$^{A17}$,Gly$^{A21}$,Lys$^{B27}$human insulin, Gln$^{B13}$,Asn$^{A21}$,Lys$^{B27}$human insulin, Gln$^{B13}$,Ser$^{A21}$,Lys$^{B27}$human insulin, Gln$^{B13}$,Thr$^{A21}$,Lys$^{B27}$human insulin, Gln$^{B13}$,Ala$^{A21}$,Lys$^{B27}$human insulin, Gln$^{B13}$,His$^{A21}$,Lys$^{B27}$human insulin, Gln$^{B13}$,Asp$^{A21}$,Lys$^{B27}$human insulin, and Gln$^{B13}$,Gly$^{A21}$,Lys$^{B27}$human insulin.

EP 214826 (Novo Nordisk), which is incorporated herein by reference, discloses rapid onset insulin compounds.

EP 194864 (Novo Nordisk), which is incorporated herein by reference, discloses insulin compounds with a prolonged action, wherein basic amino acid residues have been substituted by neutral amino acid residues. Particular mentioning is made of Gln$^{A17}$,Arg$^{B27}$,Thr$^{B30}$-NH$_2$ human insulin, Gln$^{A17}$,Gln$^{B13}$,Thr$^{B30}$-NH$_2$ human insulin, Gln$^{A17}$,Lys$^{B27}$,Thr$^{B30}$-NH$_2$ human insulin, Gln$^{A17}$,Lys$^{B27}$-NH$_2$ human insulin, Gln$^{A17}$,Gln$^{A17}$,Thr$^{B30}$-NH$_2$ human insulin, Gln$^{B13}$,Arg$^{B27}$,Thr$^{B30}$-NH$_2$ human insulin, Gln$^{B13}$,Lys$^{B27}$,Thr$^{B30}$-NH$_2$ human insulin, Gln$^{B13}$,Lys$^{B30}$-NH$_2$ human insulin, Gln$^{B13}$,Thr$^{B30}$-NH$_2$ human insulin, Arg$^{B27}$,Arg$^{B30}$-NH$_2$ human insulin, Arg$^{B27}$,Lys$^{B30}$-NH$_2$ human insulin, Arg$^{B27}$,Thr$^{B30}$-NH$_2$ human insulin, Lys$^{B27}$,Arg$^{B30}$-NH$_2$ human insulin, Lys$^{B27}$,Lys$^{B30}$-NH$_2$ human insulin, Lys$^{B27}$,Thr$^{B30}$-NH$_2$ human insulin, Lys$^{B29}$-NH$_2$,des-(B30)human insulin, Thr$^{B30}$-NH$_2$ human insulin, Lys$^{B30}$-NH$_2$ human insulin, Lys$^{B30}$(Lau)-NH$_2$ human insulin, Lys$^{B30}$,Arg$^{B31}$-NH$_2$ human insulin, Lys$^{B30}$,Lys$^{B31}$-NH$_2$ human insulin, Arg$^{B30}$-NH$_2$ human insulin, Arg$^{B30}$,Arg$^{B31}$-NH$_2$ human insulin, and Arg$^{B30}$,Lys$^{B31}$-NH$_2$ human insulin.

U.S. Pat. No. 3,528,960 (Eli Lilly), which is incorporated herein by reference, discloses N-carboxyaroyl insulin compounds in which one, two or three primary amino groups of the insulin molecule has a carboxyaroyl group.

GB Patent No. 1.492.997 (Nat. Res. Dev. Corp.), which is incorporated herein by reference, discloses insulin compounds with a carbamyl substitution at N$^{\epsilon B29}$ with an improved profile of hypoglycaemic effect.

JP laid-open patent application No. 1-254699 (Kodama Co., Ltd.), which is incorporated herein by reference, discloses insulin compounds, wherein an alkanoyl group is bound to the amino group of Phe$^{B1}$ or to the ε-amino group of Lys$^{B29}$ or to both of these.

JP laid-open patent application No. 57-067548 (Shionogi), which is incorporated herein by reference discloses insulin compounds, in which the B30 position have an amino acid having at least five carbon atoms which cannot necessarily be coded for by a triplet of nucleotides.

WO 03/053339 (Eli Lilly), which is incorporated herein by reference, disclose insulin compounds, wherein the A-chain in the N-terminal has been extended with two amino acid residues, A-1 and A0, wherein the B-chain has been extended at the N-terminal with two amino acid residues, B-1 and B0, wherein the amino acid residues at positions B28, B29 and B39 may be substituted, and wherein the ε-amino group of Lys at position B28 or B29 is covalently bound to the α-carboxyl group of a positively charged amino acid to form a Lys-Nε-aminoacid derivative. Particular mentioning is made of said analogues, wherein A-1 and B-1 are both absent, and wherein A0 represent Arg and B0 represents Arg or is absent.

Insulin compounds selected from the group consisting of: i) an analogue wherein position B28 is Asp, Lys, Leu, Val, or Ala and position B29 is Lys or Pro; and ii) des(B28-B30), des(B27) or des(B30) human insulin, are also applicable for the methods of the present invention, and in particular, the insulin compound wherein position B28 is Asp or Lys, and position B29 is Lys or Pro.

Other applicable insulin compounds are selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$ Pro$^{B29}$ human insulin, B28-N$^\epsilon$-palmitoyl Lys$^{B28}$ Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin, B29-N$^\epsilon$-(ω-carboxyheptadecanoyl) human insulin and B29-N$^\epsilon$-myristoyl-des(B30) human insulin.

Another protein which would benefit from the methods of the present invention is GLP-1. Examples of GLP-1 applicable in the methods of the present invention include human GLP-1 and GLP-1 compounds. Human GLP-1 is a 37 amino acid residue protein originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. Processing of preproglucagon to give GLP-1(7-36)-amide, GLP-1(7-37) and GLP-2 occurs mainly in the L-cells. The fragments GLP-1(7-36)-amide and GLP-1(7-37) are both glucose-dependent insulinotropic agents. In the past decades a number of structural analogues of GLP-1 were isolated from the venom of the Gila monster lizards (*Heloderma suspectum* and *Heloderma horridum*). Exendin-4 is a 39 amino acid residue protein isolated from the venom of *Heloderma horridum*, and this protein shares 52% homology with GLP-1. Exendin-4 is a potent GLP-1 receptor agonist which has been shown to stimulate insulin release and ensuring lowering of the blood glucose level when injected into dogs. The group of GLP-1 (1-37) and exendin-4(1-39) and certain fragments, analogues and derivatives thereof (designated GLP-1 compounds herein) are potent insulinotropic agents, and they are all applicable in the method of the present invention. Insulinotropic fragments of GLP-1(1-37) are insulinotropic proteins for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1 (7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogs of GLP-1(1-37) is e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analog of exendin-4(1-39) is Ser$^2$Asp$^3$-exendin-4(1-39) wherein the amino acid residues in position 2 and 3 have been replaced with serine and aspartic acid, respectively (this particular analog also being known in the art as exendin-3). Insulinotropic derivatives of GLP-1(1-37), exendin-4(1-39) and analogs thereof are what the person skilled in the art considers to be derivatives of these proteins, i.e. having at least one substituent which is not present in the parent protein molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogs thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4(1-31)-amide. Further examples of GLP-1(1-37), exendin-4(1-39), insulinotropic fragments thereof, insulinotropic analogs thereof and insulinotropic derivatives thereof are described in WO 98/08871, WO 99/43706, U.S. Pat. No. 5,424,286 and WO 00/09666, which are all enclosed herein by reference.

Another protein which would benefit from the methods of the present invention is GLP-2.

GLP-2 and GLP-2 compounds may also be modified by the methods provided by the present invention. In the present context a GLP-2 compound binds to a GLP-2 receptor, preferably with an affinity constant ($K_D$) or a potency ($EC_{50}$) of below 1 μM, e.g. below 100 nM. The term "GLP-2 compound" is intended to indicate human GLP-2 in which one or more amino acid residue has been deleted and/or replaced by another amino acid residue, natural or unnatural, and/or human GLP-2 comprising additional amino acid residues, and/or human GLP-2 in which at least one organic substituent is bound to one or more of the amino acid residues. In particular, those proteins are considered, which amino acid sequence exhibit at any sequence of 33 consecutive amino acids more than 60% of the amino acid sequence of human GLP-2. Also those proteins are considered, which amino acid sequence exhibit at any sequence of 37 consecutive amino acids more than 60% of the amino acid sequence of human GLP-2 when up to four amino acids are deleted from the amino acid sequence. Also those proteins are considered, which amino acid sequence exhibit at any sequence of 31 consecutive amino acids more than 60% of the amino acid sequence of GLP-2, when up to two amino acids are added to their amino acid sequence. The term "GLP compounds" also includes natural allelic variations that may exist and occur from one individual to another. Also, degree and location of glycosylation or other post-translation modifications may vary depending on the chosen host cells and the nature of the host cellular environment.

Candidate GLP-2 compounds, which may be used according to the present invention include the GLP-2 compounds described in WO 96/32414, WO 97/39031, WO 98/03547, WO 96/29342, WO 97/31943, WO 98/08872, which are all incorporated herein by reference.

In particular, the following GLP-2 compounds are applicable in the methods of the present invention. A2G-GLP-2(1-33); K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

GLP-2 derivatives with only one lipophilic substituent attached to the GLP-2 protein are also applicable in the methods of the present invention, such as GLP-2 derivatives wherein the lipophilic substituent comprises from 4 to 40 carbon atoms, such as from 8 to 25 carbon atoms, e.g. from 12 to 20 carbon atoms.

The following list contains GLP-2 derivatives which are particular applicable in the methods of the present invention:
S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);

L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(1-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);

L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(1-33);
D3E/L17K((S)-4-carboxy-4-(octadecanoylamino)butanoyl)/K30R/D33E-GLP-2(1-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21K(3-(hexadecanoylamino)propionyl)/K30R/D33E-GLP-2(1-33);
D3E/N24K(3-(hexadecanoylamino)propionyl)/K30R/D33E-GLP-2(1-33); and
D3E/Q28K(3-(hexadecanoylamino)propionyl)/K30R/D33E-GLP-2(1-33).

Another protein which would benefit from the methods of the present invention is Factor VII. Factor VII compounds applicable in the methods of the present invention encompasses wild-type Factor VII (i.e., a polypeptide having the amino acid sequence disclosed in U.S. Pat. No. 4,784,950), as well as variants of Factor VII exhibiting substantially the same or improved biological activity relative to wild-type Factor VII, Factor VII-related polypeptides as well as Factor VII derivatives and Factor VII conjugates. The term "Factor VII compounds" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate wild-type Factor VII, variants of Factor VII exhibiting substantially the same or improved biological activity relative to wild-type Factor VII and Factor VII-related polypeptides, in which one or more of the amino acids of the parent protein have been chemically modified, e.g. by alkylation, PEGylation, acylation, ester formation or amide formation or the like. This includes but are not limited to PEGylated human Factor VIIa, cysteine-PEGylated human Factor VIIa and variants thereof.

The term "PEGylated human Factor VIIa" means human Factor VIIa, having a PEG mole-cule modified to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

The terms "variant" or "variants", as used herein, is intended to designate Factor VII having the sequence of wild-type factor VII, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition still have FVII activity in its activated form. In one embodiment a variant is 70% identical with the sequence of wild-type Factor VII. In one embodiment a variant is 80% identical with the sequence of wild-type factor VII. In another embodiment a variant is 90% identical with the sequence of wild-type factor VII. In a further embodiment a variant is 95% identical with the sequence of wild-type factor VII.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS), all of which are incorporated herein by reference.

Particular mentioning is made of FVII variants having increased biological activity compared to wild-type FVIIa include FVII variants as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.), all of which are incorporated herein by reference, all of which are incorporated herein by reference.

Examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vase. Endovasc. Surg. 15:515-520, 1998), and Factor VIIa lacking the Gla domain, (Nicolaisen et al., FEBS Letts. 317:245-249, 1993), all of which are incorporated herein by reference.

Examples of variants of factor VII, factor VII or factor VII-related polypeptides include wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/

V158T/M298Q/S314E-FVII, F374Y/L305V/V158T/ E296V/S314E-FVII, F374Y/E296V/M298Q/K337A/ V158T/S314E-FVII, F374Y/V158D/E296V/M298Q/ K337A/S314E-FVII, F374Y/L305V/V158D/E296V/ M298Q/S314E-FVII, F374Y/L305V/E296V/M298Q/ V158T/S314E-FVII, F374Y/L305V/E296V/M298Q/ K337A/V158T-FVII, F374Y/L305V/E296V/K337A/ V158T/S314E-FVII, F374Y/L305V/M298Q/K337A/ V158T/S314E-FVII, F374Y/L305V/V158D/E296V/ M298Q/K337A-FVII, F374Y/L305V/V158D/E296V/ K337A/S314E-FVII, F374Y/L305V/V158D/M298Q/ K337A/S314E-FVII, F374Y/L305V/E296V/M298Q/ K337A/V158T/S314E-FVII, F374Y/L305V/V158D/ E296V/M298Q/K337A/S314E-FVII, S52A-F actor VII, S60A-F actor VII; R152E-Factor VII, S344A-Factor VII, Factor VIIa lacking the Gla domain; and P11Q/K33E-FVII, T106N-FVII, K143N/N145T-FVII, V253N-FVII, R290N/ A292T-FVII, G291N-FVII, R315N/N317T-FVII, K143N/ N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

Another protein which would benefit from the methods of the present invention is IL-19. Particular examples of IL-19 applicable in the methods of the present invention include those disclosed WO 98/08870 (Human Genome Science), which is incorporated herein by reference. Particular mentioning is made of the protein disclosed as SEQ ID NO:2 in WO 98/08870.

Another protein which would benefit from the methods of the present invention is IL-20. Particular examples of applicable IL-20 include those disclosed in WO 99/27103 (ZymoGenetics), which is incorporated herein by reference. In the present context, IL-20 is intended to indicate IL-20 itself and fragments thereof as well as polypeptides being at least 90% identical to IL-20 or fragments thereof. Proteins particular applicable in the methods of the present invention includes those disclosed in WO 99/27103 as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and SEQ ID NO:35.

Yet another protein which would benefit from the methods of the present invention is IL-21. Examples of IL-21 applicable in the methods of the present invention include those disclosed in WO 00/53761 (ZymoGenetics), which is incorporated herein by reference. particular mentioning is made of the protein disclosed as SEQ ID NO:2 in WO 00/53761.

Still another protein which would benefit from the methods of the present invention is TTF. TTF proteins are a family of proteins found mainly in association with the gastrointestinal tract. Particular mentioning is made of breast cancer associated pS2 protein (TFF-1), which is known from human, mouse, and rat, spasmolytical polypeptide (TFF-2), which is known from human, pig, rat, and mouse and intestinal trefoil factor (TFF-3), known from human, rat and mouse.

Other proteins from the TFF family applicable in the methods of the present invention include those disclosed in WO 02/46226 (Novo Nordisk), which is included herein by reference. Particular mentioning is made of a TFF-2 protein wherein a TFF2 protein with an amino acid as disclosed in SEQ ID NO:1 of WO 02/46226 comprising disulphide bonds between Cys6-Cys104, Cys8-Cys35, Cys19-Cys34, Cys29-Cys46, Cys58-Cys84, Cys68-Cys83, and Cys78-Cys95 and wherein a moiety X independently selected from sugar residues and oligosaccharides is covalently attached to Asn15.

Other proteins of the TFF family include TFF-1 and TFF-3 dimers as those disclosed in WO 96/06861 (Novo Nordisk), which is incorporated herein by reference.

Several melanorcortin receptors are known, and particular mentioning of proteins applicable for the methods of the present invention is made of peptidic melanocortin-4 receptor agonists, which are known to have an appetite suppressive effect. Particular mentioning is made of proteins or proteins disclosed in the following patent documents, which are all incorporated herein by reference: U.S. Pat. No. 6,054,556 (Hruby), WO 00/05263 (William Harvey Research), WO 00/35952 (Melacure), WO 00/35952 (Melacure), WO 00/58361 (Procter & Gamble), WO 01/52880 (Merck), WO 02/26774 (Procter & Gamble), WO 03/06620 (Palatin), WO 98/27113 (Rudolf Magnus Institute) and WO 99/21571 (Trega).

Other proteins or proteins applicable in the methods of the present invention include ACTH, corticotropin-releasing factor, angiotensin, calcitonin, insulin and fragments and analogues thereof, glucagon, IGF-1, IGF-2, enterogastrin, gastrin, tetragastrin, pentagastrin, urogastrin, epidermal growth factor, secretin, nerve growth factor, thyrotropin releasing hormone, somatostatin, growth hormone releasing hormone, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, asparaginase, arginase, arginine deaminase, adenosine deaminase and ribonuclease.

Proteins to be modified according to the methods of the present invention may either be isolated from natural sources (e.g. plants, animals or micro-organisms, such as yeast, bacteria, fungi or vira) or they may be synthesized. Proteins from natural sources also include proteins from transgenic sources, e.g. sources which have been genetically modified to express or to increase the expression of a protein, wherein said protein may be "natural" in the sense that it exists in nature or "unnatural" in the sense that it only exists due to human intervention. Proteins isolated form natural sources may also be subjected to synthetic modification prior to the conjugation of the present invention.

Pharmaceutical Compositions

The present invention is also directed to pharmaceutical compositions comprising a protein modified by any of the methods disclosed herein. In one aspect, such a pharmaceutical composition comprises a modified protein such as growth hormone (GH), which is present in a concentration from $10^{-15}$ mg/ml to 200 mg/ml, such as e.g. $10^{-10}$ mg/ml to 5 mg/ml and wherein said composition has a pH from 2.0 to 10.0. The composition may further comprise a buffer system, preservative(s), tonicity agent(s), chelating agent(s), stabilizers and surfactants. In one embodiment of the invention the pharmaceutical composition is an aqueous composition, i.e. composition comprising water. Such composition is typically a solution or a suspension. In a further embodiment of the invention the pharmaceutical composition is an aqueous solution. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical composition is a freeze-dried composition, whereto the physician or the patient adds solvents and/or diluents prior to use.

In another embodiment the pharmaceutical composition is a dried composition (e.g. freeze-dried or spray-dried) ready for use without any prior dissolution.

In a further aspect the invention relates to a pharmaceutical composition comprising an aqueous solution of a modified protein, such as e.g. a Modified GH protein, and a buffer, wherein said modified protein, such as e.g. Modified GH protein is present in a concentration from 0.1-100 mg/ml or above, and wherein said composition has a pH from about 2.0 to about 10.0.

In a another embodiment of the invention the pH of the composition is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof Each one of these specific buffers constitutes an alternative embodiment of the invention.

In a further embodiment of the invention the composition further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In a further embodiment of the invention the composition further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol(propyleneglycol), 1,3-propanediol, 1,3-butanediol)polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects obtained using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In a further embodiment of the invention the composition further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20th edition, 2000.

In a further embodiment of the invention the composition further comprises a stabilizer. The use of a stabilizer in pharmaceutical compositions is well-known to the skilled person. For convenience reference is made to Remington: *The Science and Practice of Pharmacy*, 20th edition, 2000.

More particularly, compositions of the invention are stabilized liquid pharmaceutical compositions whose therapeutically active components include a protein that possibly exhibits aggregate formation during storage in liquid pharmaceutical compositions. By "aggregate formation" is intended a physical interaction between the protein molecules that results in formation of oligomers, which may remain soluble, or large visible aggregates that precipitate from the solution. By "during storage" is intended a liquid pharmaceutical composition or composition once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or composition is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a protein during storage of a liquid pharmaceutical composition can adversely affect biological activity of that protein, resulting in loss of therapeutic efficacy of the pharmaceutical composition. Furthermore, aggregate formation may cause other problems such as blockage of tubing, membranes, or pumps when the protein-containing pharmaceutical composition is administered using an infusion system.

The pharmaceutical compositions of the invention may further comprise an amount of an amino acid base sufficient to decrease aggregate formation by the protein during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L or D isomer, or mixtures thereof) of a particular amino acid (methionine, histidine, arginine, lysine, isoleucine, aspartic acid, tryptophan, threonine and mixtures thereof) or combinations of these stereoisomers or glycine or an organic base such as but not limited to imidazole, may be present in the pharmaceutical compositions of the invention so long as the particular amino acid or organic base is present either in its free base form or its salt form. In one embodiment the L-stereoisomer of an amino acid is used. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the protein during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the protein acting as the therapeutic agent is a protein comprising at least one methionine residue susceptible to such oxidation. By "inhibit" is intended minimal accumulation of methionine oxidized species over time. Inhibiting methionine oxidation results in greater retention of the protein in its proper molecular form. Any stereoisomer of methionine (L or D isomer) or any combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be obtained by adding methionine such that the ratio of methionine added to methionine residues ranges from about 1:1 to about 1000:1, such as 10:1 to about 100:1.

In a further embodiment of the invention the composition further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active protein therein. Stabilizing agents of particular interest to the present invention include, but are not limited to, methionine and EDTA, which protect the protein against methionine oxidation, and a nonionic surfactant, which protects the protein against aggregation associated with freeze-thawing or mechanical shearing.

In a further embodiment of the invention the composition further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives—(e.g. sodium tauro-dihydrofusidate etc.), long-chain fatty acids and salts thereof $C_6$-$C_{12}$ (e.g. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of diproteins comprising any combination of lysine, arginine or histidine and a neutral or acidic amino acid, $N^\alpha$-acylated derivative of a triprotein comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates)monovalent surfactants, zwitterionic surfactants (e.g. N-alkyl-N,N-dimethylammonio-1-propanesulfonates, 3-cholamido-1-propyl dimethylammonio-1-propanesulfonate, cationic surfactants (quaternary ammonium bases) (e.g. cetyl-trimethylammonium bromide, cetylpyridinium chloride), non-ionic surfactants (e.g. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, $20^{th}$ edition, 2000.

It is possible that other ingredients may be present in the pharmaceutical composition of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical composition of the present invention.

Pharmaceutical compositions containing a modified protein, such as e.g. a modified GH protein according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the Modified GH protein, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions thereof, well known to those skilled in the art of phase behavior in lipid-water systems, polymeric micelles, multiple emulsions, self-emulsifying, self-microemulsifying, cyclodextrins and derivatives thereof, and dendrimers.

Compositions of the current invention are useful in the composition of solids, semisolids, powder and solutions for pulmonary administration of a modified protein, such as e.g. a Modified GH protein, using, for example a metered dose inhaler, dry powder inhaler and a nebulizer, all being devices well known to those skilled in the art.

Compositions of the current invention are specifically useful in the composition of controlled, sustained, protracting, retarded, and slow release drug delivery systems. More specifically, but not limited to, compositions are useful in composition of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles.

Methods to produce controlled release systems useful for compositions of the current invention include, but are not limited to, crystallization, condensation, co-crystallization, precipitation, co-precipitation, emulsification, dispersion, high pressure homogenization, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the modified protein, such as e.g. the Modified GH protein in the form of a nasal or pulmonal spray. As a still further option, the pharmaceutical compositions containing the modified protein, such as e.g. the Modified GH protein of the invention can also be adapted to transdermal administration, e.g. by needle-free injection or from a patch, optionally an iontophoretic patch, or transmucosal, e.g. buccal, administration.

The term "stabilized composition" refers to a composition with increased physical stability, increased chemical stability or increased physical and chemical stability. The term "physical stability" of the protein composition as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to protein aggregation, when it shows visual turbidity in daylight. Alternatively, the turbidity of the composition can be evaluated by simple turbidity measurements well-known to the skilled person. Physical stability of the aqueous protein compositions can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition as well-known by the person skilled in the art. Most proteins are prone to deamidation, a process in which the side chain amide group in glutaminyl or asparaginyl residues is hydrolyzed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment of the invention the pharmaceutical composition comprising the modified GH protein is stable for more than 6 weeks of usage and for more than 3 years of storage.

In another embodiment of the invention the pharmaceutical composition comprising the modified GH protein is stable for more than 4 weeks of usage and for more than 3 years of storage.

In a further embodiment of the invention the pharmaceutical composition comprising the Modified GH protein is stable for more than 4 weeks of usage and for more than two years of storage.

In an even further embodiment of the invention the pharmaceutical composition comprising the Modified GH protein is stable for more than 2 weeks of usage and for more than two years of storage.

Therapeutic Uses of the Modified Proteins of the Invention

To the extend that the unmodified protein is a therapeutic protein, the invention also relates to the use of the modified proteins of the invention in therapy, and in particular to pharmaceutical compositions comprising said modified proteins.

Thus, as used herein, the terms "treatment" and "treating" mean the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs. Nonetheless, it should be recognized that therapeutic, regimens and prophylactic (preventative) regimens represent separate aspects of the invention.

A "therapeutically effective amount" of a modifyied protein of the invention as used herein means an amount sufficient to cure, alleviate or partially arrest the clinical manifestations of a given disease and its complications. An amount adequate to accomplish this is defined as "therapeutically effective amount". Effective amounts for each purpose will depend on e.g. the severity of the disease or injury as well as the weight, sex, age and general state of the subject. It will be understood that determining an appropriate dosage may be achieved using routine experimentation, by constructing a matrix of values and testing different points in the matrix, which is all within the ordinary skills of a trained physician or veterinary.

The present invention thus provides a modified proteins according to the invention for use in therapy.

As such, a typical parenteral dose is in the range of $10^{-9}$ mg/kg to about 100 mg/kg body weight per administration. Typical administration doses are from about 0.0000001 to about 10 mg/kg body weight per administration. The exact dose will depend on e.g. indication, medicament, frequency and mode of administration, the sex, age and general condition of the subject to be treated, the nature and the severity of the disease or condition to be treated, the desired effect of the treatment and other factors evident to the person skilled in the art. Typical closing frequencies are twice daily, once daily, bi-daily, twice weekly, once weekly or with even longer dosing intervals. Due to the prolonged half-lifes of the compounds of the present invention compared to the corresponding un-conjugated growth hormone, a dosing regime with long dosing intervals, such as twice weekly, once weekly or with even longer dosing intervals is a particular embodiment of the invention. Many diseases, as described below, are treated using more than one medicament in the treatment, either concomitantly administered or sequentially administered. It is therefore within the scope of the present invention to use the modified proteins of the present invention in therapeutic methods for the treatment of one of the diseases described below in combination with one or more other therapeutically active compound normally used in the treatment said diseases. By analogy, it is also within the scope of the present invention to use the modified proteins of the present invention in combination with other therapeutically active compounds normally used in the treatment of one of the above mentioned diseases in the manufacture of a medicament for said disease.

Insulin is used to treat or prevent diabetes, and in one embodiment, the present invention thus provides a method of treating type 1 or type 2 diabetes, the method comprising administering to a subject in need thereof a therapeutically effective amount of an insulin or insulin compound conjugate according to the present invention. Thus, in one embodiment, the invention provides the use of a modified insulin according to the present invention in the manufacture of a medicament used in the treatment of type 1 or type 2 diabetes.

GLP-1 may be used in the treatment of hyperglycemia, type 2 diabetes, impaired glucose tolerance, type 1 diabetes, obesity, hypertension, syndrome X, dyslipidemia, β-cell apoptosis, β-cell deficiency, inflammatory bowel syndrome, dyspepsia, cognitive disorders, e.g. cognitive enhancing, neuroprotection, atherosclerosis, coronary heart disease and other cardiovascular disorders. In one embodiment, the present invention thus provides a method of treating said diseases, the method comprising administering to a subject in need thereof a therapeutically effective amount of a GLP-1 or GLP-1 compound conjugate according to the present invention. Thus, in another embodiment, the invention provides the use of a GLP-1 or GLP-1 compound conjugate according to the present invention in the manufacture of a medicament used in the treatment of the above mentioned diseases.

GLP-2 may be used in the treatment of intestinal failure leading to malabsorption of nutrients in the intestines, and in particular GLP-2 may be used in the treatment of small bowel syndrome, Inflammatory bowel syndrome, Chron's disease, colitis including collagen colitis, radiation colitis, post radiation atrophy, non-tropical (gluten intolerance) and tropical sprue, damaged tissue after vascular obstruction or trauma, tourist diarrhea, dehydration, bacteremia, sepsis, anorexia nervosa, damaged tissue after chemotherapy, premature infants, schleroderma, gastritis including atrophic gastritis, postantrectomy atrophic gastritis and helicobacter pylori gastritis, ulcers, enteritis, cul-de-sac, lymphatic obstruction, vascular disease and graft-versus-host, healing after surgical procedures, post radiation atrophy and chemotherapy, and osteoporosis. It is therefore an intension of the present invention to provide methods of treating the above diseases, the method comprising administering to a subject in need thereof a therapeutically effective amount of a GLP-2 or GLP-2 compound conjugate according to this invention. Thus, in another embodiment, the present invention provides the use of a GLP-2 or GLP-2 compound conjugate according to this invention in the manufacture of a medicament used in the treatment of the above mentioned diseases.

Compounds of the present invention also exert growth hormone activity and may as such be used in the treatment of diseases or states which will benefit from an increase in the amount of circulating growth hormone. Such diseases states include growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children. Growth hormones have also been used for acceleration of the healing of muscle tissue, nervous tissue or wounds; the acceleration or improvement of blood flow to damaged tissue; or the decrease of infection rate in damaged tissue, the method comprising administration to a patient in need thereof an effective amount of a therapeutically effective amount of a compound of formula I. The present invention thus provides a method for treating these diseases or states, the method comprising administering to a patient in need thereof a therapeutically effective amount of a growth hormone or growth hormone compound conjugate according to the present invention.

Typically, the amount of modified growth hormone administered is in the range from $10^{-7}$-$10^{-3}$ g/kg body weight, such as $10^{-6}$-$10^{-4}$ g/kg body weight, such as $10^{-5}$-$10^{-4}$ g/kg body weight.

In another embodiment, the invention provides the use of a growth hormone or growth hormone compound conjugate in the manufacture of a medicament used in the treatment of the above mentioned diseases or states.

Cytokines are implicated in the etiology of a host of diseases involving the immune system. In particular it is mentioned that IL-20 could be involved in psoriasis and its treatment, and I-21 is involved in cancer and could constitute a treatment to this disease. In one embodiment, the invention provides a method for the treatment of psoriasis comprising the administration of a therapeutically effective amount of a IL-20 conjugate according to the present invention. In another embodiment, the invention relates to the use of an IL-20 conjugate of the present invention in the manufacture of a medicament used in the treatment of psoriasis.

In another embodiment, the present invention relates to a method of treating cancer, the method comprising administration of a therapeutically effective amount of a IL-21 conjugate of the present invention to a subject in need thereof.

In another embodiment, the invention relates to the use of an IL-21 conjugate according to the present invention in the manufacture of a medicament used in the treatment of cancer.

TTF proteins may be used to increase the viscosity of muscus layers in subject, to reduce secretion of salvia, e.g. where the increase salvia secretion is caused by irradiation therapy, treatment with anticholinergics or Sjögren's syndrome, to treat allergic rhinitis, stress induced gastric ulcers secondary to trauma, shock, large operations, renal or liver diseases, treatment with NSAID, e.g. aspirin, steroids or alcohol. TTF proteins may also be used to treat Chron's disease, ulcerative colitis, keratoconjunctivitis, chronic bladder infections, intestinal cystitis, papillomas and bladder cancer. In one embodiment, the invention thus relates the a method of treating the above mention diseases or states, the method comprising administering to a subject patient in need thereof a therapeutically effective amount of a TTF conjugate according to the present invention.

In another embodiment, the invention relates the use of a TTF conjugate of the present invention in the manufacture of a medicament for the treatment of the above mentioned diseases or states.

Melanocortin receptor modifiers, and in particular melanorcortin 4 receptor agonists have been implicated the treatment and prevention of obesity and related diseases. In one embodiment, the present invention provides a method for preventing or delaying the progression of impaired glucose tolerance (IGT) to non-insulin requiring type 2 diabetes, for preventing or delaying the progression of non-insulin requiring type 2 diabetes to insulin requiring diabetes, for treating obesity and for regulating the appetite. Melanocortin 4 receptor agonists have also been implicated in the treatment of diseases selected from atherosclerosis, hypertension, diabetes, type 2 diabetes, impaired glucose tolerance (IGT), dyslipidemia, coronary heart disease, gallbladder disease, gall stone, osteoarthritis, cancer, sexual dysfunction and the risk of premature death. In one embodiment, the invention thus provides a method of treating the above diseases or states, the method comprising administering to a subject in need thereof a therapeutically effective amount of an melanocortin 4 receptor agonist conjugate of the present invention.

In still another embodiment, the invention relates to the use of a melanocortin 4 receptor agonist conjugate of the present invention in the manufacture of a medicament for the treatment of the above mentioned diseases or states.

Factor VII compounds have been implicated in the treatment of disease related to coagulation, and biological active Factor VII compounds in particular have been implicated in the treatment of hemophiliacs, hemophiliacs with inhibitors to Factor VIII and IX, patients with thrombocytopenia, patients with thrombocytopathies, such as Glanzmann's thrombastenia platelet release defect and storage pool defects, patient with von Willebrand's disease, patients with liver disease and bleeding problems associated with traumas or surgery. Biologically inactive Factor VII compounds have been implicated in the treatment of patients being in hypercoagluable states, such as patients with sepsis, deep-vein thrombosis, patients in risk of myocardial infections or thrombotic stroke, pulmonary embolism, patients with acute coronary syndromes, patients undergoing coronary cardiac, prevention of cardiac events and restenosis for patient receiving angioplasty, patient with peripheral vascular diseases, and acute respiratory distress syndrome. In one embodiment, the invention thus provides a method for the treatment of the above mentioned diseases or states, the method comprising administering to a subject in need thereof a therapeutically effective amount of a Factor VII compound conjugate according to the present invention.

In another embodiment, the invention provides the use of a Factor VII compound conjugate according to the present invention in the manufacture of a medicament used in the treatment of the above mentioned diseases or states.

Many diseases are treated using more than one medicament in the treatment, either concomitantly administered or sequentially administered. It is therefore within the scope of the present invention to use the modified proteins of the present invention in therapeutic methods for the treatment of one of the above mentioned diseases in combination with one or more other therapeutically active compound normally used to in the treatment said disease. By analogy, it is also within the scope of the present invention to use the modified proteins of the present invention in combination with other therapeutically active compounds normally used in the treatment of one of the above mentioned diseases in the manufacture of a medicament for said disease.

As discussed above, therapeutic modified proteins according to the methods of the present invention may be used in therapy, and this is also an embodiment of the present invention.

In another embodiment, the present invention provides the use of modified proteins of the present invention in diagnostics.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise embodimented. No language in the specification should be construed as indicating any non-embodimented element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the embodiments appended hereto as permitted by applicable law.

The invention is further illustrated by the following non-limiting examples.

EXAMPLES

The TGase used in the examples is microbial transglutaminase from *Streptoverticillium mobaraense* according to U.S. Pat. No. 5,156,956.

The examples also contain the following general methods:
Capillary Electrophoresis Capillary electrophoresis was carried out using an Agilent Technologies 3DCE system (Agilent Technologies). Data acquisition and signal processing were performed using Agilent Technologies 3DCE ChemStation. The capillary was a 64.5 cm (56.0 cm efficient length) 50 µm i.d. "Extended Light Path Capillary" from Agilent. UV detection was performed at 200 nm (16 nm Bw, Reference 380 nm and 50 nm Bw). The running electrolyte was phosphate buffer 50 mM pH 7 (method A). The capillary was conditioned with 0.1M NaOH for 3 min, then with Milli-Q water for 2 min and with the electrolyte for 3 min. After each run, the capillary was flushed with milli-Q water for 2 min, then with phosphoric acid for 2 min, and with milli-Q water for 2 min. The hydrodynamic injection was done at 50 mbar for 4.0 s. The voltage was +25 kV. The capillary temperature was 30 C and the runtime was 10.5 min.

Maldi-Tof Mass Spectrometry

Molecular weights were determined using the Autoflex Maldi-Tof instrument (Bruker). Samples were prepared using alfa-cyano-4-hydroxy-cinnamic acid as matrix.

RP-HPLC

RP-HPLC analysis was performed on a Agilent 1100 system using a Vydac 218TP54 4.6 mm×250 mm 5 µm C-18 silica column (The Separations Group, Hesperia). Detection was by UV at 214 nm, 254 nm, 280 nm and 301 nm. The column was equilibrated with 0.1% trifluoracetic acid/$H_2O$ and the sample was eluted by a suitable gradient of 0 to 90% acetonitrile against 0.1% trifluoracetic acid/$H_2O$.

LC-MS

LC-MS analysis was performed on a PE-Sciex API 100 or 150 mass spectrometer equipped with two Perkin Elmer Series 200 Micropumps, a Perkin Elmer Series 200 autosampler, a Applied Biosystems 785A UV detector and a Sedex 75 Evaporative Light scattering detector. A Waters Xterra 3.0 mm×50 mm 5µ C-18 silica column was eluted at 1.5 ml/min at room temperature. It was equilibrated with 5% acetonitrile/0.1% trifluoracetic acid/$H_2O$ and eluted for 1.0 min with 5% acetonitrile/0.1% trifluoracetic acid/$H_2O$ and then with a linear gradient to 90% acetonitrile/0.1% trifluoracetic acid/$H_2O$ over 7 min. Detection was by UV detection at 214 nm and Evaporative light Scattering. A fraction of the column eluate was introduced into the ionspray interface of a PE-Sciex API 100 mass spectrometer. The mass range 300-2000 amu was scanned every 2 seconds during the run.

Quantification of Protein

Protein concentrations were estimated by measuring absorbance at 280 nm using a NanoDrop ND-1000 UV-spectrophotometer.

Enzymatic Peptide Mapping for Determation of Site(s) of Derivatization

Peptide mapping was performed using Asp-N digestion of the reduced and alkylated protein. First the protein was treated with DTT (Dithiothreitol) and iodoacetamide according to standard procedures. The alkylated product was purified using HPLC. Subsequently the alkylated purified product was digested overnight with endoprotease Asp-N (Boehringer) at an enzyme:substrate ratio of 1:100. The digest was HPLC separated using a C-18 column and standard trifluoracetic acid/acetonitrile buffer system. The resulting peptide map was compared to that of un-derivatized hGH and fractions with different retention times were collected and further analyzed using Maldi-tof mass spectrometry.

SDS Page

SDS poly-acrylamide gel electrophoresis was performed using NuPAGE 4%-12% Bis-Tris gels (Invitrogen NP0321BOX). The gels were silver stained (Invitrogen LC6100) or Coomassie stained (Invitrogen LC6065) and where relevant also stained for PEG with barium iodide as described by M. M. Kurfurst in *Anal. Biochem.* 200(2):244-248, 1992.

Protein Chromatography

Protein chromatography was performed on an Äkta Explorer chromatographic system and columns from GE Health Care. Anion exchange was done using a Q-Sepharose HP 26/10 column. Starting buffer was 20 mM triethanolamine buffer pH 8.5 and eluting buffer was starting buffer +0.2M NaCl. The compounds were typically eluted with a gradient of 0-75% eluting buffer over 15 column volumes. De-salting and buffer exchange was performed using a HiPrep 26/10 column.

Examples

The TGase used in the examples is microbial transglutaminase from *Streptoverticillium mobaraense* according to U.S. Pat. No. 5,156,956.

The examples also contain the following general methods:
Capillary Electrophoresis Capillary electrophoresis was carried out using an Agilent Technologies 3DCE system (Agilent Technologies). Data acquisition and signal processing were performed using Agilent Technologies 3DCE ChemStation. The capillary was a 64.5 cm (56.0 cm efficient length) 50 μm i.d. "Extended Light Path Capillary" from Agilent. UV detection was performed at 200 nm (16 nm Bw, Reference 380 nm and 50 nm Bw). The running electrolyte was phosphate buffer 50 mM pH 7 (method A). The capillary was conditioned with 0.1M NaOH for 3 min, then with Milli-Q water for 2 min and with the electrolyte for 3 min. After each run, the capillary was flushed with milli-Q water for 2 min, then with phosphoric acid for 2 min, and with milli-Q water for 2 min. The hydrodynamic injection was done at 50 mbar for 4.0 s. The voltage was +25 kV. The capillary temperature was 30 C and the runtime was 10.5 min.

Maldi-Tof Mass Spectrometry

Molecular weights were determined using the Autoflex Maldi-Tof instrument (Bruker). Samples were prepared using alfa-cyano-4-hydroxy-cinnamic acid as matrix.

RP-HPLC

RP-HPLC analysis was performed on a Agilent 1100 system using a Vydac 218TP54 4.6 mm×250 mm 5 μm C-18 silica column (The Separations Group, Hesperia). Detection was by UV at 214 nm, 254 nm, 280 nm and 301 nm. The column was equilibrated with 0.1% trifluoracetic acid/H$_2$O and the sample was eluted by a suitable gradient of 0 to 90% acetonitrile against 0.1% trifluoracetic acid/H$_2$O.

LC-MS

LC-MS analysis was performed on a PE-Sciex API 100 or 150 mass spectrometer equipped with two Perkin Elmer Series 200 Micropumps, a Perkin Elmer Series 200 autosampler, a Applied Biosystems 785A UV detector and a Sedex 75 Evaporative Light scattering detector. A Waters Xterra 3.0 mm×50 mm 5μ C-18 silica column was eluted at 1.5 ml/min at room temperature. It was equilibrated with 5% acetonitrile/ 0.1% trifluoracetic acid/H$_2$O and eluted for 1.0 min with 5% acetonitrile/0.1% trifluoracetic acid/H$_2$O and then with a linear gradient to 90% acetonitrile/0.1% trifluoracetic acid/H$_2$O over 7 min. Detection was by UV detection at 214 nm and Evaporative light Scattering. A fraction of the column eluate was introduced into the ionspray interface of a PE-Sciex API 100 mass spectrometer. The mass range 300-2000 amu was scanned every 2 seconds during the run.

Quantification of Protein

Protein concentrations were estimated by measuring absorbance at 280 nm using a NanoDrop ND-1000 UV-spectrofotometer.

Enzymatic Peptide Mapping for Determation of Site(s) of Derivatization

Peptide mapping was performed using Asp-N digestion of the reduced and alkylated protein. First the protein was treated with DTT (Dithiothreitol) and iodoacetamide according to standard procedures. The alkylated product was purified using HPLC. Subsequently the alkylated purified product was digested overnight with endoprotease Asp-N (Boehringer) at an enzyme:substrate ratio of 1:100. The digest was HPLC separated using a C-18 column and standard trifluoracetic acid/acetonitrile buffer system. The resulting peptide map was compared to that of un-derivatized hGH and fractions with different retention times were collected and further analyzed using Maldi-tof mass spectrometry.

SDS Page

SDS poly-acrylamide gel electrophoresis was performed using NuPAGE 4%-12% Bis-Tris gels (Invitrogen NP0321BOX). The gels were silver stained (Invitrogen LC6100) or Coomassie stained (Invitrogen LC6065) and where relevant also stained for PEG with barium iodide as described by M. M. Kurfurst in *Anal. Biochem.* 200(2):244-248, 1992.

Protein Chromatography

Protein chromatography was performed on an Äkta Explorer chromatographic system and columns from GE Health Care. Anion exchange was done using a Q-Sepharose HP 26/10 column. Starting buffer was 20 mM triethanolamine buffer pH 8.5 and eluting buffer was starting buffer +0.2M NaCl. The compounds were typically eluted with a gradient of 0-75% eluting buffer over 15 column volumes. De-salting and buffer exchange was performed using a HiPrep 26/10 column.

Example 1

Preparation of Modified Human Growth Hormone (Compound 1)

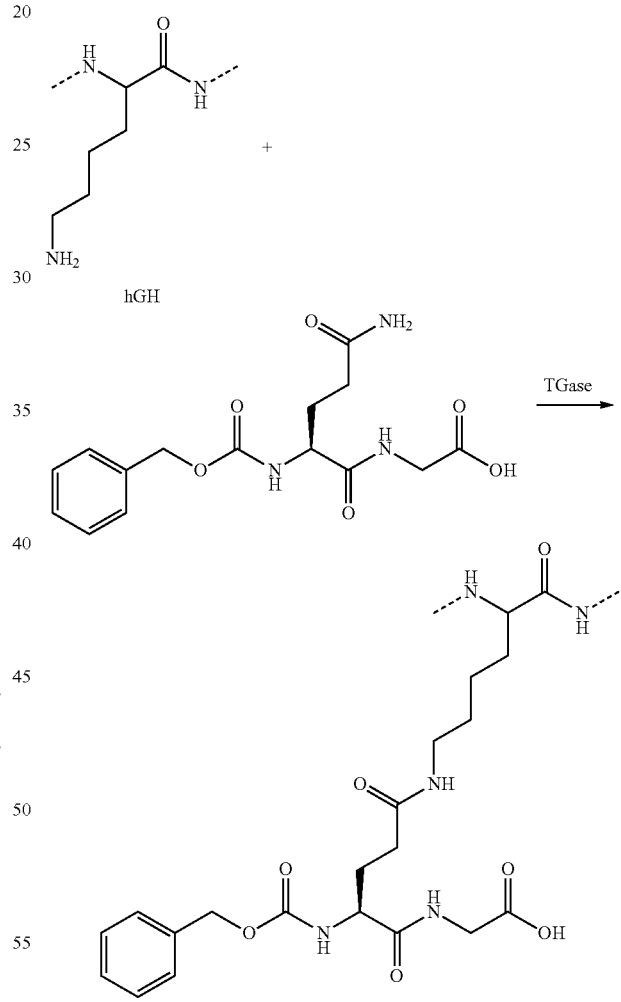

Compound 1

Figure 3:
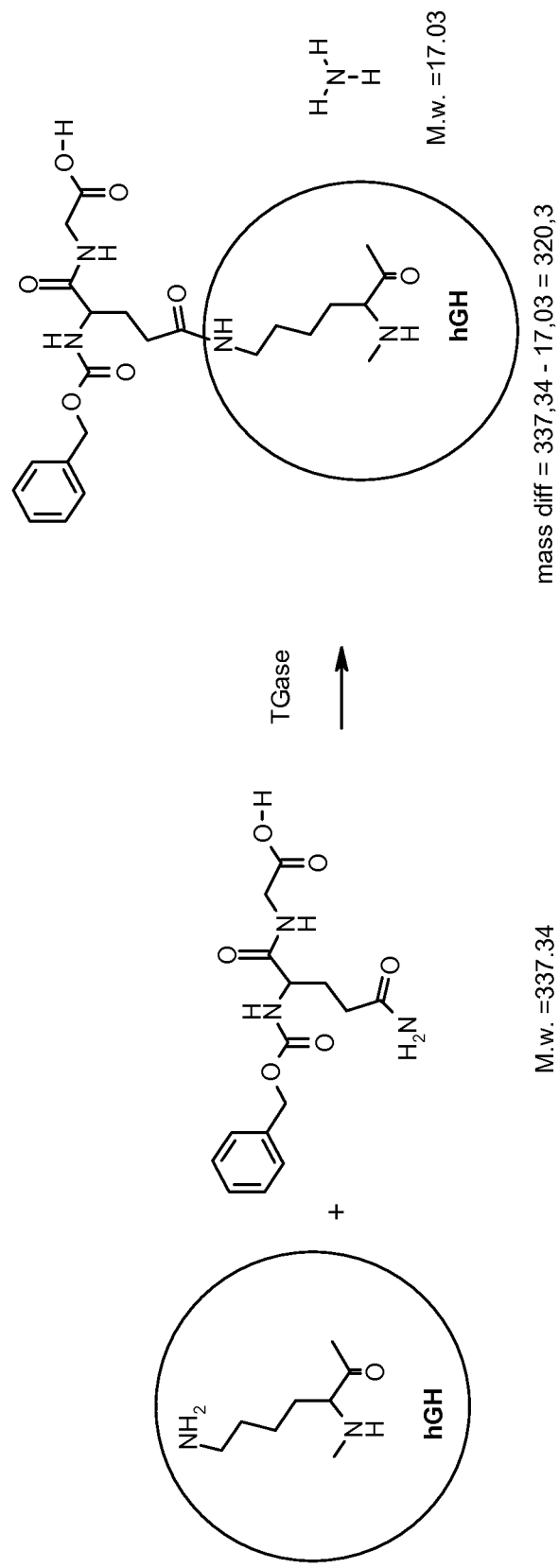
"
FIG. 3 depicts the modification of human growth hormone as described in Example 1.

As depicted in FIG. 3, 20 mM Triethanolamine buffer, pH 8.5, is prepared. (TEA-buffer); (a) 20 mg hGH is dissolved in TEA-buffer (0.5 ml), and (b) 68 mg Z-Gln-Gly-OH is dissolved in TEA-buffer (1 ml); and (c) 200 mg Aktiva WM TGase preparation (containing ~0.5% TGase protein) is dissolved in TEA-buffer (1 mL). (A) and (B) are mixed and 10 μl (C) is added. After 19 h at room temp the main product is isolated by ion exchange chromatography and peptide mapping and sequence analysis shows that the product is selectively derivatized in Lys145.

Example 2

Preparation of N-carbonyloxybenzyl-glutaminyl-glycyl-(4-amino-phenylalanine) [Z-Gln-Gly-(4-amino-Phe)-OH], Compound 2

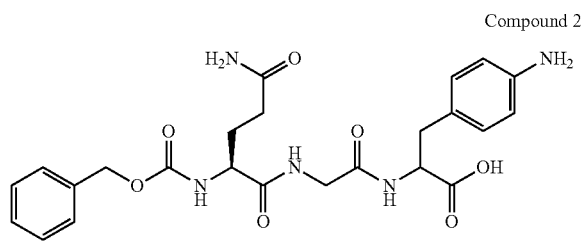 [SMILES: NC(=O)CC[C@H](NC(=O)OCc1ccccc1)C(=O)NCC(=O)NC(Cc1ccc(N)cc1)C(=O)O]

Compound 2

Attachment of the first amino acid to the resin: To a 2-chlorotrityl chloride resin (Pepchem, 2 g, 1.5 mmol/g) was added Fmoc-(4-Boc-amino-Phe)-OH (Fluka, 2.26 g, 4.5 mmol) dissolved in a mixture of DCM (16 ml) and diisopropylethylamine (780 µl). The slurry was stirred for 5 min followed by addition of diisopropylethylamine (1540 µl). Stirring was continued for a period of 1 h after which methanol (5 ml) was added, and stirring was continued for additional 15 min. The resin was drained and washed with dichloromethane (DCM) (6×30 ml) followed by N-methylpyrrolidone (NMP) (6×30 ml).

Removal of the Fmoc group: To the resin was added 20% piperidine in NMP (20 ml) and left reacting for 15 min. The resin was drained and again treated with 20% piperidine in NMP (20 ml) for 1 h. The resin was drained and washed with NMP (6×30 ml). Coupling Z-Gln-Gly-OH: To the resin was added a solution of Z-Gln-Gly-OH (Bachem, 1.52 g, 4.5 mmol) and hydroxybenzotriazole (HOBt, 0.61 g, 4.5 mmol) in NMP followed by diisopropylcarbodiimide (DIC) (700 µl, 4.5 mmol). After reaction overnight, the resin was drained and washed with NMP (6×30 ml), then with DCM (6×30 ml).

Cleavage from the solid support: The resin was drained to remove bulk DCM. It was treated with a mixture of trifluoroacetic acid (TFA) (12.6 ml), water (0.6 ml), DCM (5.8 ml) and triisopropylsilane (0.8 ml). After reaction for 1 h, the resin was filtered slowly within 15 min into diethylether (100 ml) which was stirred for an additional 30 min. The resulting precipitate was recovered by centrifugation and washed 3 times with diethylether. The solid was dried overnight in vacuo. The product was pure and homogenous according to $^1$H-NMR and LC-MS.

Example 3

Transamidation of hGH with Z-Gln-Gly-(4-amino-Phe)-OH (compound 2) to obtain Z-Gln(hGH)-Gly-(4-amino-Phe)-OH, Compound 3

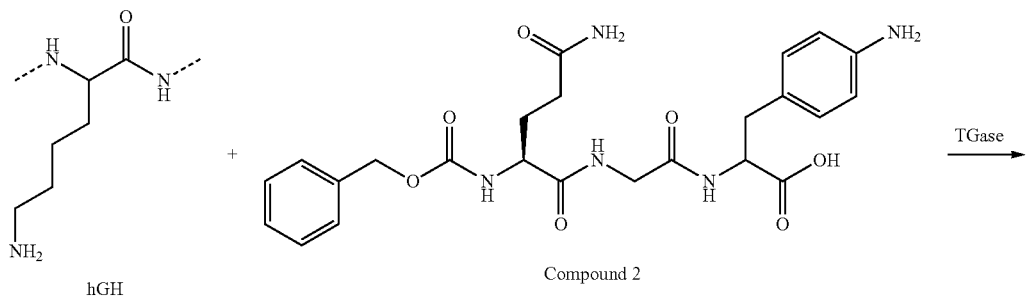

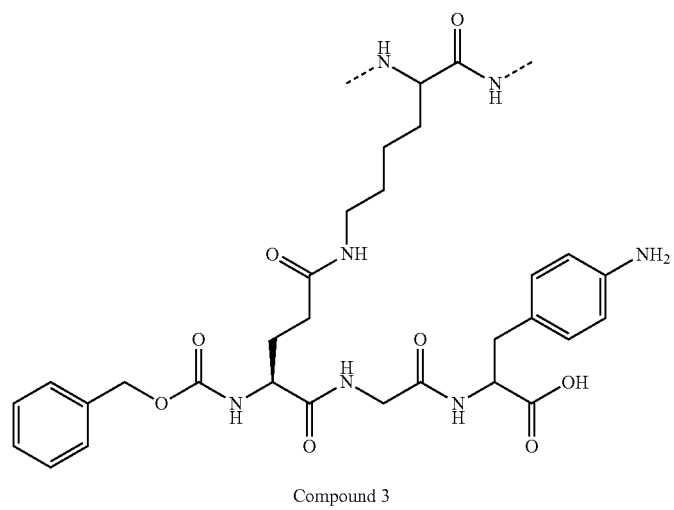

Compound 3

Three solutions are prepared: 1) hGH (40 mg, 1.8 µmol) dissolved in 1 ml 20 nM triethanolamine buffer pH 8.5; 2) Z-Gln-Gly-OH (202 mg, 412 µmol) dissolved in 2 ml 20 nM triethanolamine buffer pH 8.5, pH adjusted to 8.15 using 10% triethanolamine solution (2.4 ml); 3) Transglutaminase Activa WM (Ajinomoto) (1% in solid mixture with maltodextrin, 36 mg, 9 nmol) was dissolved in 1 ml 20 nM triethanolamine buffer pH 8.5.

Solutions 1 and 2 were mixed and 111 µl of solution 3 was added to this mixture; pH was 8.2 and volume 5.5 ml. The reaction was monitored by CE. After 5 h reaction at r.t., Analysis by CE showed the presence of a new product with an increased migration time, showing about 70% conversion to the transamidated product. To the reaction mixture was added 10 mM aqueous N-ethylmaleimide (300 µl) and it was stored at 5° C. overnight. The mixture was loaded to a 15 ml HiPrep column (GE Healthcare) and eluted using triethanolamine buffer pH 8.5 to remove low molecular weight substances and salt. Relevant fractions were pooled and the recovery was 36.6 mg protein based on UV absorption measurements.

Example 4

PEGylation of Z-Gln(hGH)-Gly-(4-amino-Phe)-OH (Compound 3) to obtain compound 4

To the solution of transamidated hGH prepared according to Example 3 was added a mixture of glacial acetic acid (1 ml) and water (1 ml). pH was measured to 2 and was subsequently adjusted to 3.3 using 1 M NaOH (1 ml). To this solution was added PEG-aldehyde 40 kDa (120 mg, 3 µmol) dissolved in a mixture of triethanolamine buffer pH 8.5 (1.2 ml) and water (1.2 ml). It was allowed to react for a period of 1 h, after which 70 µl of a solution of NaCNBH$_3$ (7.1 mg, 8 µmol) in water (1 ml) was added. Reaction was continued overnight. Analysis by reduced SDS PAGE showed the presence of a product with the expected molecular weight. The mixture was desalted on a HiPrep column as Example 3, recovering the relevant pooled fractions as 20 ml which were diluted with 20 ml water. This mixture was loaded to a Q-Sepharose HP 26/10 (GE Healthcare). The starting buffer was triethanolamine buffer pH 8.5. The product was eluted using a gradient of 0-75% 0.2 M NaCl in triethanolamine buffer pH 8.5 in 15 column volumes, subsequently 75-100% 0.2 M NaCl in triethanolamine buffer pH 8.5 in 5 column volumes.

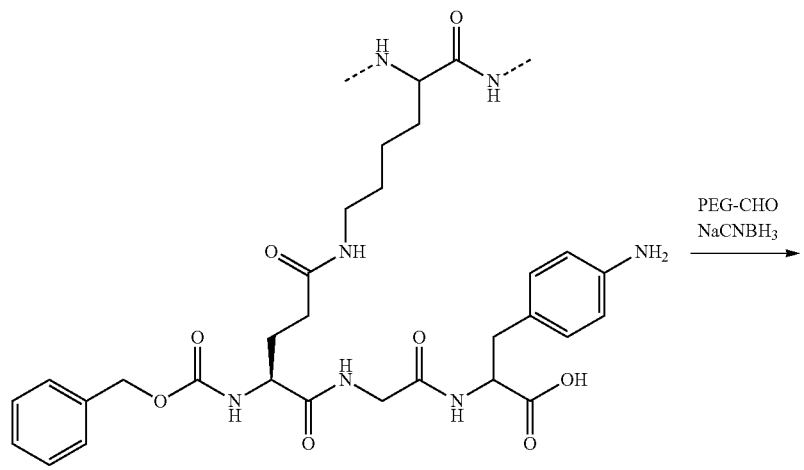

Compound 3

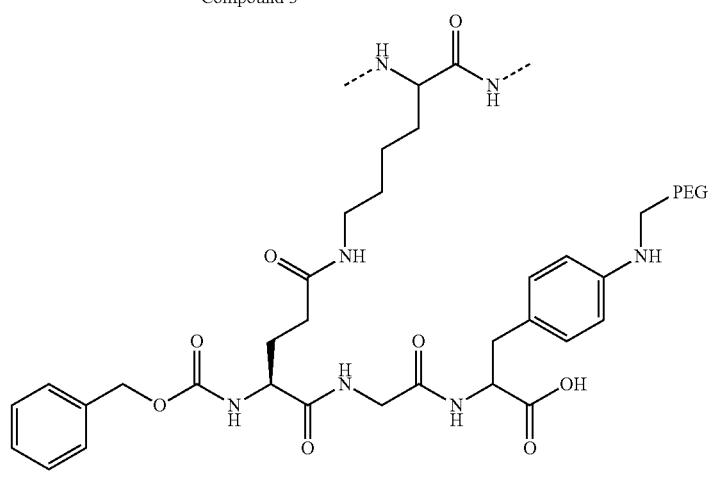

Compound 4

Peptide mapping analysis and sequence analysis confirmed that compound 4 was hGH selectively modified in position Lys145.

Example 5

Preparation of N-carbonyloxybenzyl-glutaminyl-glycine-2,3-dihydroxypropan-1-amide, Compound 5

A solution of Z-Gln-Gly-OH (Bachem, 1 g, 2.96 mmol) in DMF (20 ml) with triethylamine (0.41 ml) was prepared under nitrogen atmosphere and cooled to <20° C. Isobutylchloroformiate (407 µl, 0.42 g, 3.1 mmol) dissolved in DMF (4 ml) was added to the stirred solution dropwise over a period of 3 min. The stirring was continued in the cold for another 50 min after which a suspension of (R)-3-amino-1,2-propanediol (0.27 g, 2.96 mmol) in DMF (2 ml) with triethylamine (0.41 ml) was added. The cooling bath was removed allowing the solution slowly to reach room temperature. Stirring was continued for another 16 h after which the reaction mixture was concentrated to dryness in vacuo leaving the crude product (1.9 g) which was purified by reversed phase HPLC. The product was pure and homogenous according to $^1$H-NMR and LC-MS.

Example 6

Preparation of N-carbonyloxybenzyl-glutaminyl-glycyl-propargylglycine, Compound 6

This compound was prepared analogously to Compound 2 (Example 2) using Fmoc-propargylglycine instead of Fmoc-(4-Boc-amino-Phe)-OH as the first amino acid to be coupled to the resin.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

Example 7

Transamidation of hGH with Z-Gln-Gly-2,3-dihydroxypropan-1-amide (compound 5) to obtain Z-Gln(hGH)-Gly-2,3-dihydroxypropan-1-amide, Compound 7

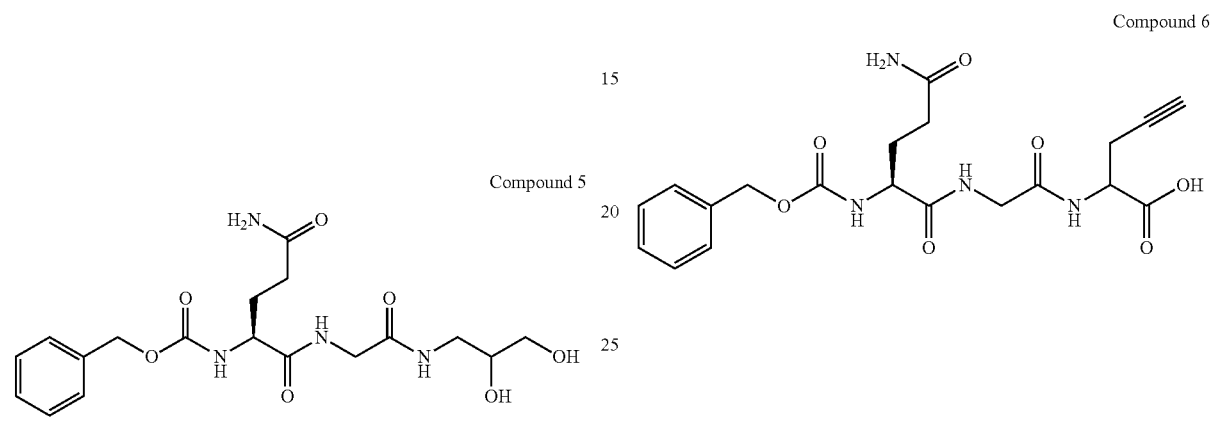

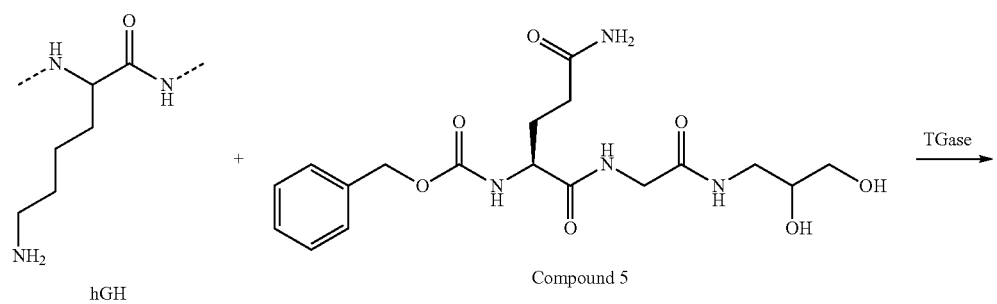

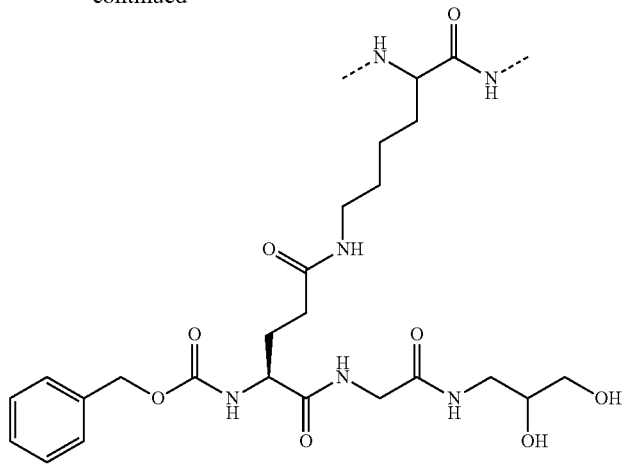

Compound 7

The procedure was identical to that of example 3. After a period of 25 hours, 65% of the starting material (hGH) was converted into the desired product 7, as determined by CE analysis.

Example 8

Transamidation of hGH with Z-Gln-Gly-propargylglycine-OH (compound 6) to obtain Z-Gln(hGH)-Gly-propargylglycine-OH, Compound 8

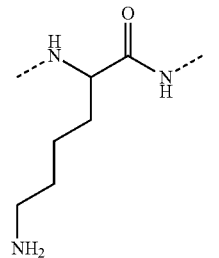

hGH

+

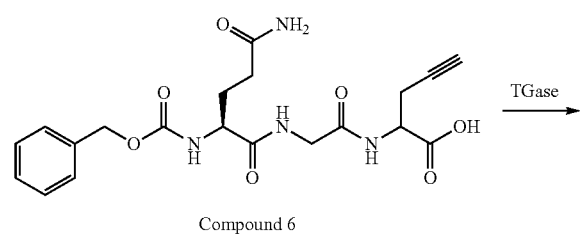

Compound 6

Compound 8

The procedure was identical to that of example 3. After a period of 22 hours, 59% of the starting material (hGH) was converted into the desired product 8, as determined by CE analysis.

SEQUENCES

SEQ ID NO: 1
Human Growth Hormone Polynucleotide

```
atggctacag gctcccggac gtccctgctc ctggcttttg gcctgctctg cctgccctgg cttcaagagg gcagtgcctt cccaaccatt cccttatcca ggcttttga caacgctatg ctccgcgccc atcgtctgca ccagctggcc tttgacacct accaggagtt tgaagaagcc tatatcccaa aggaacagaa gtattcattc ctgcagaacc cccagaccct cctctgtttc tcagagtcta ttccgacacc ctccaacagg gaggaaacac aacagaaatc caacctagag ctgctccgca tctccctgct
```

-continued

```
gctcatccag tcgtggctgg agcccgtgca gttcctcagg agtgtcttcg ccaacagcct ggtgtacggc gcctctgaca gcaacgtcta tgacctccta aaggacctag aggaaggcat ccaaacgctg atggggaggc tggaagatgg cagcccccgg actgggcaga tcttcaagca gacctacagc aagttcgaca caaactcaca acgatgac gcactactca agaactacgg gctgctctac tgcttcagga aggacatgga caaggtcgag acattcctgc gcatcgtgca gtgccgctct gtggagggca gctgtggctt ctag
```

SEQ ID NO: 2
Human Growth Hormone Polypeptide
matgsrtsll lafgllclpw lqegsafpti plsrlfdnam lrahrlhqla fdtyqefeea yipkeqkysf lqnpqtslcf sesiptpsnr eetqqksnle llrisllliq swlepvqflr svfanslvyg asdsnvydll kdleegiqtl mgrledgspr tgqifkqtys kfdtnshndd allknyglly cfrkdmdkve tflrivqcrs vegscgf SEQ ID NO: 3
MAAGSRTSLLLAFGLLCLSWLQEGSAFPTIPLSRLFDNAMLRARRLYQLA
YDTYQEFNPQTSLCFSESIPTPSNRVKTQQKSNLELLRISLLLIQSWLEP
VQLLRSVFANSLVYGASDSNVYRHLKDLEEGIQTLMWRLEDGSPRTGQIF
NQSYSKFDTKSHNDDALLKNYGLLYCFRKDMDKVETFLRIVQCRSVEGSC
GF

---

What is claimed is:

1. A method for site selective modification of a protein, said method comprising: contacting the protein with an auxiliary protein and a property modifying group selected from the group consisting of

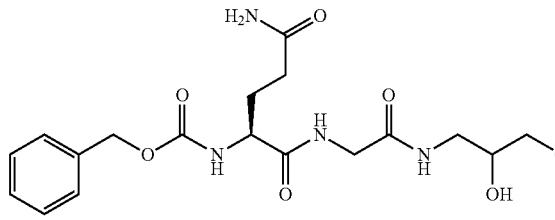

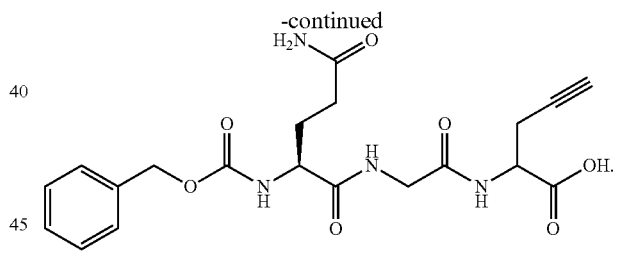

2. The method according to claim 1, wherein the protein subject to site selective modification is a cytokine.

3. The method according to claim 1, wherein the protein subject to site selective modification belongs to class of 4-helix bundle proteins.

4. The method according to claim 1, wherein the protein subject to site selective modification is hGH.

5. The method according to claim 1, wherein the auxiliary protein is an enzyme that modifies glutamine residues.

6. The method according to claim 1, wherein the auxiliary protein is a transglutaminase.

7. The method according to claim 6, in which the transglutaminase is microbial transglutaminase from *S. mobaraense*.

8. The method according to claim 7, wherein the transglutaminase is a mutant of microbial transglutaminase from *S. mobaraense* with 80% or more sequence homology relative to native microbial transglutaminase from *S. mobaraense*.

9. A method for site selective modification of growth hormone, the method comprising contacting growth hormone

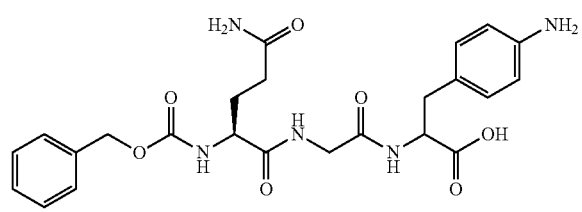

with an auxiliary protein and a property modifying group selected from the group consisting of

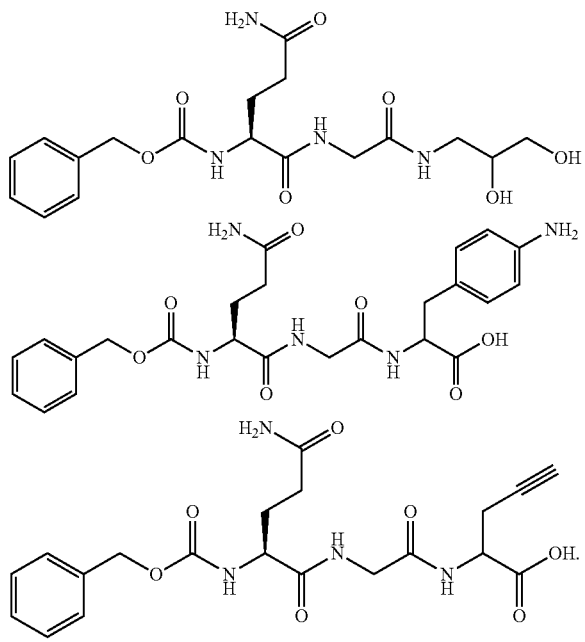

10. The method according to claim 9, wherein the growth hormone is human growth hormone.

11. The method according to claim 9, wherein the auxiliary protein is a transglutaminase.

12. The method according to claim 11, in which the transglutaminase is microbial transglutaminase from *S. mobaraense*.

13. The method according to claim 12, wherein the transglutaminase is a mutant of microbial transglutaminase from *S. mobaraense* with 80% or more sequence homology relative to native microbial transglutaminase from *S. mobaraense*.

14. The method according to claim 10, wherein the human growth hormone is modified at a lysine residue.

15. The method according to claim 14, wherein the human growth hormone is site selectively modified at lysine 145, wherein said lysine 145 corresponds to the amino acid at position 145 of SEQ ID NO:4.

16. The method according to claim 15, wherein the human growth hormone is site selectively modified at lysine 145 and subsequently conjugated to a protracting group that prolongs the in vivo halflife of the conjugate compared to hGH.

17. The method according to claim 16, wherein the protracting group is a hydrophilic polymer.

18. The method according to claim 16, wherein the protracting group is a PEG.

19. The method according to claim 16, wherein the protracting group contains a moiety that binds reversibly to albumin.

20. The method according to claim 16, wherein the protracting group contains a fatty acid residue or a fatty diacid residue.

* * * * *

UNITED STATES PATENT AND TRADEMARK OFFICE
CERTIFICATE OF CORRECTION

PATENT NO. : 8,586,532 B2  
APPLICATION NO. : 12/674291  
DATED : November 19, 2013  
INVENTOR(S) : Buchardt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this  
Seventh Day of April, 2015

Michelle K. Lee  
*Director of the United States Patent and Trademark Office*